US006214628B1

(12) United States Patent
Lakowicz et al.

(10) Patent No.: US 6,214,628 B1
(45) Date of Patent: Apr. 10, 2001

(54) METHOD OF CONDUCTING AN ASSAY OF A SAMPLE CONTAINING AN ANALYTE OF INTEREST

(75) Inventors: Joseph R. Lakowicz, 10037 Fox Den Rd., Ellicott City, MD (US) 21042; Felix Castellano, Columbia; Zakir Murtaza, Baltimore, both of MD (US)

(73) Assignee: Joseph R. Lakowicz, Ellicott City, MD (US)

( * ) Notice: Subject to any disclaimer, the term of this patent is extended or adjusted under 35 U.S.C. 154(b) by 0 days.

(21) Appl. No.: 09/007,167

(22) Filed: Jan. 14, 1998

(51) Int. Cl.$^7$ .................. G01N 33/53; G01N 33/536; G01N 33/533; G01N 21/64; G06K 9/00
(52) U.S. Cl. .................. 436/518; 436/172; 436/138; 436/546; 436/800; 436/536; 436/537; 436/68; 436/133; 436/163; 436/166; 436/74; 436/8; 435/4; 435/968; 435/7.1; 435/7.93; 435/7.5; 435/501; 435/536; 435/546; 435/164; 435/172; 435/94; 435/63; 422/82.07
(58) Field of Search .................. 435/4, 968, 7.1, 435/7.5, 501, 536, 7.21, 546, 164, 172, 94, 95, 63; 422/82.07, 82.08, 82.09; 436/172, 518, 138, 546, 800, 536, 537, 68, 133, 163, 166, 74, 8; 382/6, 58, 191, 128, 133, 312, 129; 128/633, 634, 635; 250/461.2, 458.1, 459.1, 200, 338.1; 315/169.3; 356/73, 317, 318, 417, 346, 39

(56) References Cited

U.S. PATENT DOCUMENTS

| | | | | |
|---|---|---|---|---|
| 4,454,317 | * | 6/1984 | Disteldorf et al. | 544/193 |
| 4,735,907 | * | 4/1988 | Schaeffer et al. | 436/534 |
| 4,819,658 | * | 4/1989 | Kolodner | 128/736 |
| 5,246,867 | * | 9/1993 | Lakowicz et al. | 436/95 |
| 5,281,825 | * | 1/1994 | Berndt et al. | 250/458.1 |
| 5,485,530 | | 1/1996 | Lakowicz et al. | 382/191 |
| 5,580,527 | * | 12/1996 | Bell et al. | 422/82.07 |
| 5,624,847 | * | 4/1997 | Lakowicz et al. | 436/68 |
| 5,628,310 | * | 5/1997 | Rao et al. | 128/633 |
| 5,631,169 | * | 5/1997 | Lakowicz et al. | 436/537 |
| 5,648,269 | * | 7/1997 | Lakowicz et al. | 436/68 |
| 5,660,991 | * | 8/1997 | Lakowicz et al. | 435/7.1 |
| 5,759,767 | * | 6/1998 | Lakowicz et al. | 435/4 |
| 5,780,319 | * | 7/1998 | Wilson et al. | 436/518 |

FOREIGN PATENT DOCUMENTS 4439 347 * 1/1996 (DE) .............. C07K/16/00

OTHER PUBLICATIONS

Guo et al., A Long–lived, highly luminescent Re(I) Metal–Ligand Complex as a Biomolecular Probe., Analytical Biochemistry 254, 179–186 (1997), article No. AB972413, Jul. 1997.*
merriam Webster's Collegiate Dictionary, Tenth Edition, p. 567, Jul. 1997.*
Joseph R. Lakowicz et al., Fluorescence Lifetime Imaging, Analytical Biochemistry 202, pp. 316–330, (1992).

* cited by examiner

*Primary Examiner*—Long V. Le
*Assistant Examiner*—Lisa J. Cook
(74) *Attorney, Agent, or Firm*—Rothwell, Figg, Ernst & Manbeck, p.c.

(57) ABSTRACT

In accordance with the present invention, a method of conducting an assay of a sample containing an analyte of interest includes the step of forming a mixture so as to bring a metal-ligand complex into interactive proximity with the sample containing the analyte of interest. The mixture is irradiated with electromagnetic light energy so as to cause emission of light indicative of the analyte of interest. The emitted light is measured, and the measurement of the emitted light is utilized to measure the analyte of interest. The metal-ligand complex can be $[Re(bcp)(CO)_3(4\text{-}COOHPy)]^+$, $[Os(phen)_2(aphen)]^{2+}$, $[Os(tpy)(triphos)]^{2+}$, $[Os(tppz)_2]^{2+}$, and $[Os(ttpy)_2]^{2+}$, or the like. Also, the present invention is directed to a metal-ligand complex of the formula $[Re(bcp)(CO)_3(4\text{-}COOHPy)]^+$.

15 Claims, 29 Drawing Sheets

2,2':6,2"-terpyridine (tpy,3)

5-amino-phenanthroline (aphen)

Pyridine (py,1)

4-methyl,2,2'-bipyridine-4'-carboxylic acid (mcbpy,2)

Bis(2-diphenylphosphinoethyl)phenyl phosphine (triphos)

4-tolyl, 2,2':6,2"-terpyridine (ttpy)

2,3,5,6-tetrakis(2-pyridyl)pyrazine(tppz)

METHOD OF CONDUCTING AN ASSAY OF A SAMPLE CONTAINING AN ANALYTE OF INTEREST

BACKGROUND OF THE INVENTION

1. Field of the Invention

The present invention is in the field of conducting an assay of a sample containing an analyte of interest.

2. Description of the Background Art

In recent years there has been increased interest in the synthesis, characterization and application of metal-ligand complexes in biomolecule research. In addition to their use as photosensitizers, metal-ligand complexes have been used as luminescence probes in polymers. For instance, metal-containing intercalators such as square-planar platinum(II) complexes containing aromatic terpyridine or phenanthroline ligands have been used in probing DNA structure and the intercalation process itself. The reagent methidiumpropyl-Fe(II) EDTA, which contains a redox-active metal center tethered to an organic intercalator, has been applied in "footprinting" experiments to determine the sequence specificity of small drugs bound to DNA. Ru(II) and Os(II) transition metal compounds have been used to probe DNA structure and study long-range electron transfer.

More recent studies have shown that ruthenium (Ru(II)), rhenium (Re(I)) and osmium (Os(II)) metal-ligand complexes display high anisotropy in the absence of rotational diffusion. Importantly, metal ligand complexes display luminescence decay times ranging from 100 ns to 100 $\mu$s. Consequently, these probes extend the observable timescale of anisotropy decay measurements by orders of magnitude compared with that observable with routinely used organic fluorophores. As a result of this, metal-ligand complexes have been used to probe the microsecond dynamics of DNA. In addition, time-resolved anisotropy measurements of proteins can be extended to the microsecond timescale using metal-ligand complexes. Intensity and anisotropy decays of Ru(II) metal-ligand complexes when covalently linked to human serum albumin, concanavalin A, human immunoglobulin G and ferritin demonstrated that this class of probes could be used to measure rotational motions from 10 ns to 1.5 $\mu$s, which so far has been inaccessible using the classical organic fluorophores. Fluorescence polarization immunoassays using metal-ligand complexes covalently bound to human serum albumin (as the antigen) demonstrated the potential use of metal-ligand complexes in fluorescence polarization immunoassays of high-molecular-weight analytes.

Fluorescence polarization (FP) was first theoretically described by Perrin in 1926, which was subsequently expanded and measured by Weber. Dandliker and co-workers adapted FP for use in analytical biochemistry including antigen (Ag)-antibody (Ab) interactions, and hormone-receptor interactions. Since establishment of the theory and method by Dandliker, the use of FPI's (fluorescence polarization immunoassays) for the quantitative and qualitative measurement of various types of molecules and bioconjugates has been reported. These include therapeutic drug monitoring, determination of hormones, drugs of abuse, proteins and peptides, proteases and inhibitors, as well as DNA binding interactions. In fact, FPI technology is presently in widespread commercial use in several instruments.

A serious limitation of present immunoassays is that they are limited to low molecular weight antigens. This limitation is a result of the use of fluorophores, such as fluorescein, which display lifetimes near 4 ns. A FPI requires that emission from the unbound labeled antigen be depolarized, so that an increase in polarization may be observed upon antigen binding to antibody. For depolarization to occur, the antigen must display a rotational correlation time much shorter than the lifetime of the probe (in the case of fluorescein, less than 4 ns) which limits the dynamic range of the FPI to antigens with low molecular weights (FIG. 16). Some long lifetime fluorophores, such as chelates of $Eu^{3+}$ and $Tb^{3+}$ have been used in time-resolved immunoassays, but they do not display polarized emission and are thus not useful in FPI's.

More recent studies have shown that $[Ru(bpy)_2(dcb)]^{2+}$, where bpy is 2,2'-bipyridine and dcb is 4,4'-dicarboxylic acid-2,2'-bipyridine, displays high polarization in the absence of rotational diffusion (~0.25), as well as a long lifetime (~400 ns). The experimental results demonstrated that the steady-state polarization of $[Ru(bpy)_2(dcb)]^{2+}$ labeled to HSA was sensitive to the binding of anti-HSA, which resulted in a 200% increase in polarization. Another metal-ligand complex, $[Os(bpy)_2(dcb)]^{2+}$, was also used in a FPI to detect a high molecular weight bioconjugate using red excitation and emission wavelengths.

Many different approaches have been used to circumvent the present limitation of FPI's to low molecular weight substances. An early attempt to develop FPI's for high molecular weight antigens was reported by Grossman. The dansyl (dimethylaminonaphthalene sulfonic acid) fluorophore was used because of its lifetime near 20 ns. Tsuruoka and coworkers attempted to develop a FPI with IgG by increasing the molecular weight of the antibody. This was accomplished by immobilizing the antibody with latex or colloidal silver. Urios and Cittanova decreased the size of the labeled antibody by using Fab fragments in place of complete IgG molecules. Another approach to enable the measurement of high-molecular-weight antigens was introduced by Wei and Herron. They used a tetramethylrhodamine-labeled synthetic peptide, which has a high binding affinity for the Ab of hCG (human chorionic gonadotrophin), as the tracer antigen in their FPI for hCG. In the assay, the tracer antigen, which has a low molecular weight, is replaced by hCG (high molecular weight) thus reducing the amount of polarization.

Since the basic theory of the depolarization of fluorescence through Brownian rotation was presented by Perrin in 1926, fluorescence anisotropy decay measurements have been widely used to study the rotational dynamics of proteins, membrane-bound proteins and other macromolecules. The use of the polarization of extrinsic fluorescent labels to study proteins was introduced by Weber and was applied to the characterization of a number of proteins by Weber and others.

There are limitations imposed by the short fluorescence lifetime that have been circumvented by use of phosphorescence anisotropy decays, which have been used to study the rotational dynamics of membrane-bound proteins. Such measurements are based exclusively on the triplet probe eosin, which displays a millisecond phosphorescence decay time in the absence of oxygen. Rotational motions have been quantified by transient absorption anisotropy and by time-resolved phosphorescence anisotropy. There are, however, relatively few useful triplet probes. The use of phosphorescence is also inconvenient because of the need to rigorously exclude molecular oxygen, and the low initial phosphorescence anisotropies, typically 0.1 or smaller.

The polarized luminescence from metal ligand complexes has been used to study macromolecular dynamics. Studies have shown that ruthenium (Ru), rhenium (Re) and osmium (Os) metal ligand complexes display high anisotropy in the absence of rotational diffusion. Importantly, these metal ligand complexes display luminescence decay times ranging from 100 ns to 100 μs. Consequently, these probes extend the observable timescale of anisotropy decay measurements by many-fold compared with that observable with routinely used fluorophores. As a result, metal ligand complexes have been used to measure rotational motion of proteins and probe the submicrosecond dynamics of DNA. Time-resolved anisotropy measurements have demonstrated that metal ligand complexes when covalently linked to human serum albumin (HSA), concanavalin A, human immunoglobin G, and ferritin can be used to measure rotational motions on the 10 ns to 1.5 μs timescale.

Conventional organic fluorophores typically have a lifetime in the range of 1–10 ns, generally absorb in the high energy range, and are not very photostable. These properties limit the ability of these fluorophores to study slower domain-to-domain motions in proteins or the rotational motions of membrane-bound proteins. Furthermore the sensitivity of these fluorophores is also limited by interfering autofluorescence which also occurs at the 1–10 ns time scale.

There remains a need in the art for metal-ligand complex probes which display long absorption emission wavelengths, long lifetimes, high luminescence, and/or high quantum yields, for use as biomolecular probes, and/or for metal-ligand complex probes that can be used in fluorescence polarization immunoassays of high molecular weight analytes, and for metal-ligand complex probes that can be used as anisotropy probes for protein hydrodynamics.

SUMMARY OF THE INVENTION

In accordance with the present invention, a method of conducting an assay of a sample containing an analyte of interest includes the step of forming a mixture so as to bring a metal-ligand complex into interactive proximity (10 to 120 Å) with the sample containing the analyte of interest. The mixture is irradiated with electromagnetic light so as to induce emission of light indicative of the analyte of interest. The emitted light is measured, and the measurement of the emitted light is utilized to measure the analyte of interest. In accordance with one embodiment, the metal-ligand complex is selected from the group consisting of $[Re(bcp)(CO)_3(4\text{-}COOHPy)]^+$, $[Os(phen)_2(aphen)]^{2+}$, $[Os(tpy)(triphos)]^{2+}$, $[Os(tppz)_2]^{2+}$, and $[Os(ttpy)_2]^{2+}$.

As used herein, "bcp" is 2,9-dimethyl-4,7-diphenyl-1,10 phenanthroline; "4-COOHPy" is isonicotinic acid; "phen" is 1,10 phenanthroline; "aphen" is 5-amino-1,10 phenanthroline; "tpy" is 2,2':6,2"-terpyridine; "triphos" is bis(2-diphenylphosphinoethyl)-phenyl phosphine; "tppz" is 2,3,5,6-tetrakis(2-pyridyl)pyrazine; and "ttpy" is 4-tolyl,2,2':6,2"-terpyridine.

DETAILED DESCRIPTION OF THE INVENTION

Figure 1:
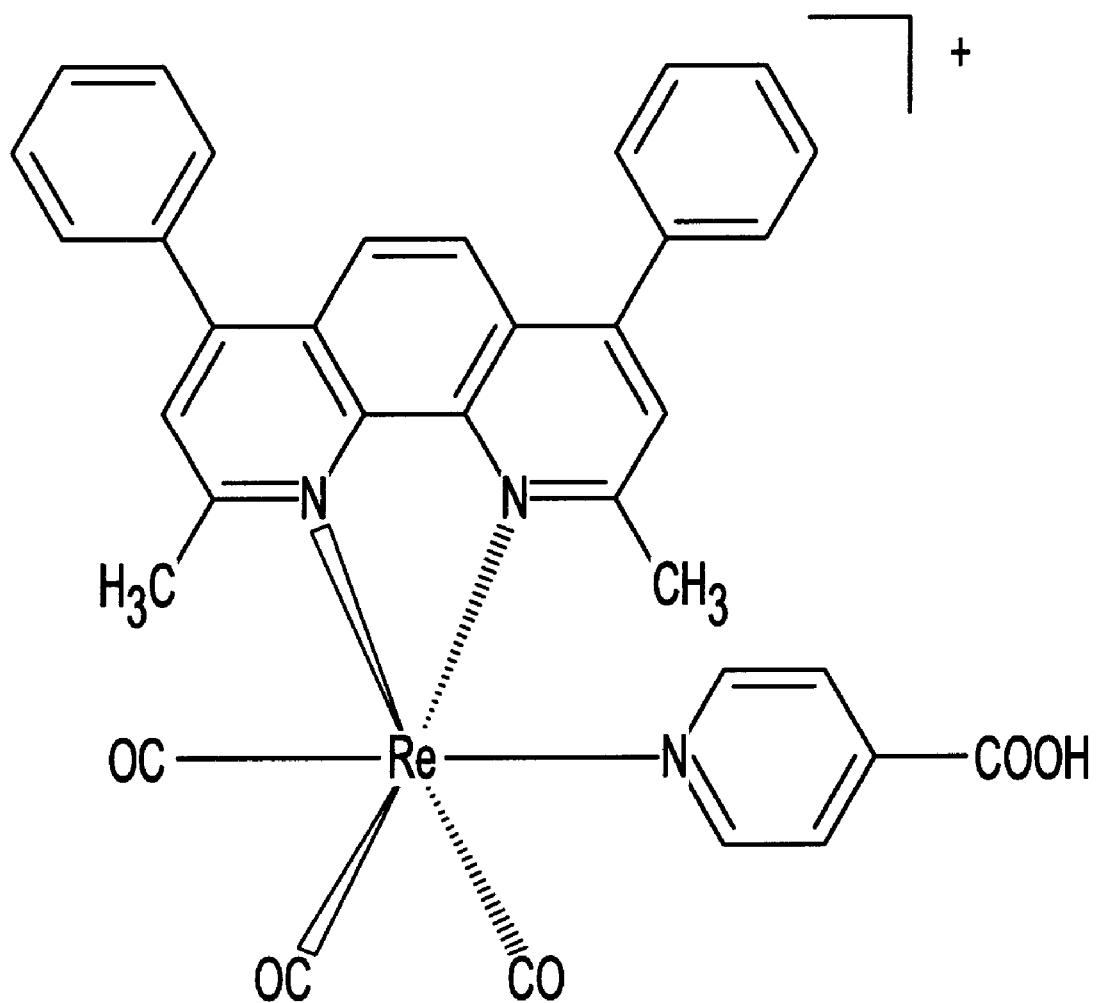
FIG. 1 shows the molecular structure of $[Re(bcp)(CO)_3(4\text{-}COOHPy)]^+$, which displays a high quantum yield near 0.5 in organic solutions and a lifetime near 7 μs.

Metal-ligand complexes offer advantages for optical sensing because they allow lifetime based sensing with low cost instrumentation. Many of these complexes display polarized emission. Polarized emission is valuable because it enables these compounds to be used for polarization immunoassays.

The metal-ligand complex probes of the invention have applications in biophysics, clinical chemistry, and immunoassays. The complexes of the platinum metals, Ru(II), Os(II), and Re(I), display anisotropy properties that can be successfully utilized in fluorescence polarization immunoassays and in studies of protein and/or lipid hydrodynamics. The complexes can be comprised of mono, bis, or tris (heteroleptic) complexes of Ru(II) and Os(II) and carbon monoxide diimine complexes of Re(I). The metal-ligand complexes include the high quantum yield rhenium (I) complex of the formula [Re(bcp)(CO)$_3$(4-COOHPy)]$^+$ and the long lifetime osmium (II) complexes, [Os(phen)$_2$(aphen)]$^{2+}$, [Os(tpy)(triphos)]$^{2+}$, [Os(tppz)$_2$]$^{2+}$, and [Os(ttpy)$_2$]$^{2+}$.

The ligands covalently bound to the metals can include ligands based on diimine, phosphine, arsine, pyridine, substituted pyridines, carbon monoxide, carbonyl, and any combination thereof. The ligands may be substituted with functional groups that can be directly conjugated to macromolecules such as amine reactive N-hydroxysuccidimide, isothiocyante, sulfonyl chloride containing ligands, sulfhydryl reactive iodoacetamide, and maleimide containing ligands.

These long lifetime metal-ligand complexes offer advantages for optical sensing because they allow lifetime based sensing with low cost instrumentation. These new probes can be used in biophysical chemistry, immunoassays of high molecular weight antigens, with red laser diode, red LED, or blue or ultraviolet LED excitation, and in lifetime immunoassays with improved spectral properties.

[Re(bcp)(CO)$_3$(4-COOHPy)]$^+$ displays a quantum yield and lifetime considerably longer than that available with previous metal-ligand complexes. The lifetimes of [Os(phen)$_2$(aphen)]$^{2+}$, [Os(tpy)(triphos)]$^{2+}$, [Os(tppz)$_2$]$^{2+}$, and [Os(ttpy)$_2$]$^{2+}$ are longer than that available with previous osmium complexes.

A favorable property of [Re(bcp)(CO)$_3$(4-COOHPy)]$^+$ is that it is not as severely quenched by oxygen in aqueous solution when bound to biological molecules. The lifetimes of rhenium labeled DPPG vesicles can exceed 3 μs in oxygenated aqueous solution, and their quantum yield is 0.2 or larger in oxygenated solutions. This rhenium (I) complex displays a four fold higher quantum yield and an eight fold longer lifetime compared to prior art rhenium (I) complexes. Rhenium labeled HSA is only moderately quenched by dissolved oxygen, and the average lifetime is near 3 μs.

[Os(phen)$_2$(aphen)]$^{2+}$ and [Os(tpy)(triphos)]$^{2+}$ display a quantum yield of 0.02, which is larger than the quantum yield of previous osmium complexes, in which the quantum yield was less than 0.001.

The absorption spectra of [Os(phen)$_2$(aphen)]$^{2+}$, [Os(tpy)(triphos)]$^{2+}$, [Os(tppz)$_2$]$^{2+}$, and [Os(ttpy)$_2$]$^{2+}$ extend to 700 nm which allows them to be used with long wavelength excitation. The emission of these osmium (II) complexes above 650 nm is desirable for avoiding autofluorescence from biological samples and for use with non-invasive transdermal sensing. The high anisotropy of these osmium complexes near 0.3 makes them useful in fluorescence polarization immunoassays. It is desirable to have probes which display long absorption emission wavelengths and also display long lifetimes. The lifetime of [Os(tppz)$_2$]$^{2+}$ is near 150 ns, which is 10-fold larger than obtained with prior art osmium (II) complexes, which displayed a lifetime of 14 ns. The long lifetime permits such probes to be used with gated detection to avoid interfering autofluorescence.

Luminescence probes have high sensitivity and specificity. Luminescence probes based on metal-ligand complexes are valuable in biochemistry and biophysics.

The invention is applicable to long-lived, highly luminescent rhenium (I) metal-ligand complexes as biomolecular probes.

The newly synthesized rhenium(I) metal-ligand complex [Re(bcp)(CO)$_3$(4-COOHPy)], where bcp is 2,9-dimethyl-4, 7-diphenyl-1,10-phenanthroline and 4-COOHPy is isonicotinic acid, exhibits high quantum yields, long lifetimes, and high anisotropy in the absence of rotational diffusion, and can be conjugated to proteins and lipids.

The flexibility in selection of the metal and the ligand renders metal-ligand complexes a versatile class of biomolecular probes. A wide range of lifetimes, absorption and emission spectra, and polarization characteristics offers numerous experimental opportunities in biophysics and clinical chemistry. For instance, a long lifetime is desirable for fluorescence polarization immunoassays of high-molecular-weight antigens, whereas a long wavelength is favorable for non-invasive clinical applications, due to lower autofluorescence and higher tissue transmission at longer wavelengths.

With its high quantum yields, long lifetimes, as well as its highly polarized emission, this rhenium (I) complex may expand the measurement of rotational motions to timescales>10 $\mu$s when bound to macromolecules.

The use of such metal-ligand complexes enable fluorescence polarization immunoassays to bypass the usual limitation to low-molecular-weight antigens. The usual limitation is a consequence of the <10 ns decay times of the previously used fluorophores.

The invention is also applicable to fluorescence polarization immunoassays of high molecular weight analytes.

Figure 16:
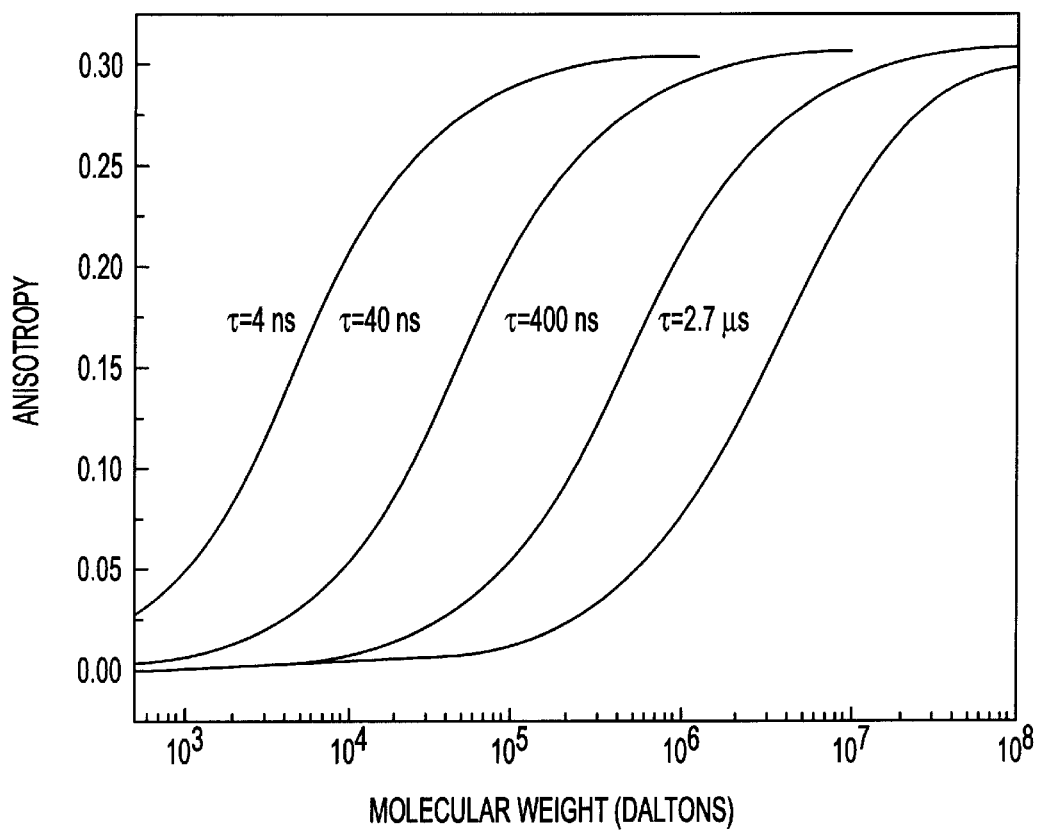
FIG. 16 graphically shows molecular weight dependent anisotropy for a protein-bound luminophore with luminescence lifetimes of 4, 40, 400, and 2700 ns.
Figure 17A:
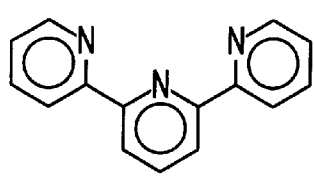
FIG. 17 shows the molecular structures of the ligands in $[Os(phen)_2(aphen)]^{2+}$, $[Os(tpy)(triphos)]^{2+}$, $[Os(tppz)_2]^{2+}$, and $[Os(ttpy)_2]^{2+}$.
Figure 17B:
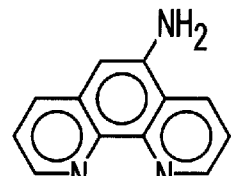
Figure 17C:
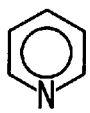
Figure 17D:
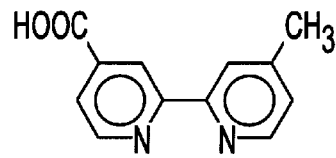
Figure 17E:
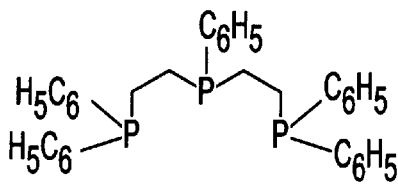
Figure 17F:
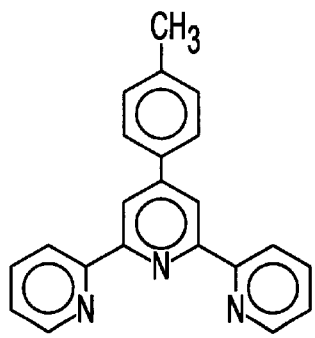
Figure 17G:
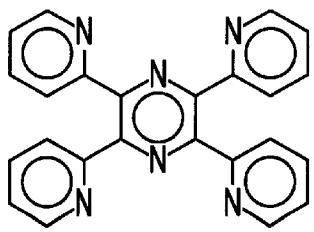

A new FPI probe, [Re(bcp)(CO)$_3$(4-COOHPy)](ClO$_4$), for high molecular weight antigens has been synthesized. This Re(I) complex displays highly polarized emission (with a maximum polarization near 0.4 and maximum anisotropy near 0.3) in the absence of rotational diffusion and a long average lifetime (2.7 $\mu$s) when bound to proteins in air-equilibrated aqueous solution. The steady-state polarization of the Re(I) complex labeled HSA conjugate (Re-HSA) was sensitive to the binding of anti-HSA, resulting in a significant increase in luminescence polarization. The labeled HSA was also used in a competitive format with unlabeled HSA acting as an antigen. More importantly, the lifetime of this probe when covalently labeled to HSA in air-equilibrated aqueous solution is near 3 $\mu$s, which theoretically allows immunoassays of antigens with molecular weights up to $10^8$ Daltons (FIG. 16).

The fluorescence polarization (P) of a labeled macromolecule depends on the fluorescence lifetime ($\tau$) and the rotational correlation time ($\theta$):

$$\left(\frac{1}{P} - \frac{1}{3}\right) = \left|\frac{1}{P_0} - \frac{1}{3}\right|\left(1 + \frac{\tau}{\theta}\right) \quad (1)$$

where P$_0$ is the polarization observed in the absence of rotational diffusion. The effect of molecular weight on the polarization values can be seen from an alternative form of Equation 1:

$$\left(\frac{1}{P} - \frac{1}{3}\right) = \left(\frac{1}{P_0} - \frac{1}{3}\right)\left(1 + \frac{kT}{\eta V}\tau\right) \quad (2)$$

where k is the Boltzmann constant, T is the absolute temperature in Kelvin, $\eta$ is the viscosity of the solution, and V is the molecular volume. The molecular volume of the protein is related to the molecular weight (M$_r$) and the rotational correlation time by:

$$\theta = \frac{\eta V}{kT} = \frac{\eta M_r}{RT}(\bar{v} + h) \quad (3)$$

where R is the ideal gas constant, $\bar{v}$ is the specific volume of the protein, and h is the hydration, typically 0.2 g H$_2$O/1 g protein. Generally, the observed correlation times are about twofold longer than those calculated for an anhydrous sphere (Eq. 3 with h=0) due to the effects of hydration and the nonspherical shapes of most proteins. Therefore, in aqueous solution at 20° C. ($\eta$=1 cP), one can expect a protein such as HSA (M$_r$~65,000 Da, with $\bar{v}$+h=1.9) to display a rotational correlation time near 50 ns.

The advantage of using a luminophore with a long lifetime is illustrated by comparing the expected polarization values for materials with different molecular weights, labeled with probes with different lifetimes, FIG. 16. It is convenient to use the anisotropy (r) in this calculation. The anisotropy and polarization are related by:

$$P = \frac{I_\| - I_\perp}{I_\| + I_\perp} \quad (4)$$

$$r = \frac{I_\| - I_\perp}{I_\| + 2I_\perp} \quad (5)$$

where I$_\|$ and I$_\perp$ are the vertically and horizontally polarized components of the emission. The values of P and r can be interchanged using:

$$r = \frac{2P}{3-P} \quad (6)$$

$$P = \frac{3r}{2+r} \quad (7)$$

The parameters P and r are both commonly used to describe rotational diffusion processes of fluorophores in solution. The values of P are more often used in FPI because they are entrenched by tradition and are slightly larger than the anisotropy values. The parameter r is preferred on the basis of theory. The anisotropy of a labeled macromolecule is:

$$r = \frac{r_0}{1 + \tau/\theta} \quad (8)$$

where r$_0$ is the anisotropy in the absence of rotational diffusion and is typically near 0.3 for most fluorophores, although the theoretical limit given colinear transition dipoles for absorption and emission is 0.4.

The expected anisotropy values for a range of photoluminescence lifetimes were simulated. These calculations were based on Equations 3 and 8, $\bar{v}$ established on the assumptions that the limiting anisotropy (r$_0$) was 0.3 in the absence of rotational diffusion, the solution viscosity was 1 cP, and +h=1.9 for the protein. These simulations demonstrate how the lifetime of the luminophore determines the range of molecular weights which can be resolved by the luminophore in an immunoassay. Presently, most immunoassays rely on fluorescein and rhodamine derivatives as fluorescent probes ($\tau$~4 ns). If one considers that most low molecular weight antigens are in the range of <1000 Da, the expected anisotropy of the labeled antigen can be estimated from FIG. 16 to be in the range of 0.05. Upon antigen association with antibody, the molecular weight increases (Mr ~160,000 Da) and the anisotropy of the bioconjugate approaches 0.30. Hence, a large change in anisotropy is found upon binding of Ag to Ab for low molecular weight antigens, when utilizing a 4 ns lifetime fluorophore.

However, if the molecular weight of the labeled antigen is larger, above 20,000 Da, then the anisotropy changes only slightly upon binding to antibody, if the same fluorophore is used. For instance, suppose the molecular weight of the labeled antigen is 160,000 Da, with a rotational correlation time of 125 ns, and that of the antibody-bound form is 600,000 Da, with a rotational correlation time of 470 ns. In this particular case, the anisotropy values will differ by less than 2% between the two forms using a short lifetime fluorophore. This small change is attributed to the large discrepancy between the lifetime of the fluorophore and the rotational correlation time of the labeled macromolecular complex. It is this reason why FPI's are performed only in the low molecular weight range with conventional short lifetime fluorophores.

The lifetime of the luminophore $[Re(bcp)(CO)_3(4\text{-}COOHPy)]^+$ is in the range of 3 $\mu s$. For the example described above, the binding assay would now be detectable using luminescence polarization (FIG. 16). Theoretically, a luminophore with a lifetime of 3 $\mu s$ could allow the analysis of biological systems with molecular weights up to 100 million Daltons and correlation times up to 80 $\mu s$, thereby greatly expanding the capabilities of FPI's to include the study of entire cells, viruses, and other large biomolecules and biomolecular complexes.

The superior approach for the direct measurement of high molecular weight analytes in an immunoassay is to develop luminescence probes with lifetimes that are comparable to the rotational correlation times of the antibody, antigen, and the bioconjugates they form. The use of the photoluminescence from metal-to-ligand charge transfer (MLCT) excited states in this regard is definitely the proper direction of this research. The sensitivity and dynamic range of a generic immunoassay can be correlated well to the lifetime of the probe used and the hydrodynamic volumes (molecular weight) of the bound and free tracer antigen (FIG. 16). To observe comparable anisotropy values for a 2.7 $\mu s$ probe as that of a 4 ns probe, the molecular weight range can be at least 3 orders of magnitude larger in the former case.

Two disadvantages of MLCT complexes are their low extinction coefficients and quantum yields when compared to a probe like fluorescein. The extinction coefficients of MLCT compounds are generally 2–5 fold lower than fluorescein. There is generally about a 10-fold difference in quantum yield between fluorescein and MLCT compounds. However, these disadvantages are offset by the fact that the photostability of MLCT complexes is remarkable compared to fluorescein, and MLCT compounds do not display any probe—probe interactions, quite unlike fluorescein, which allows for a much larger dye:protein ratio when labeling with MLCT complexes. In addition, the long-lifetimes of MLCT complexes allow for the off-gating of the autofluorescence from biological samples which takes place in the 1—10 ns timescale, which is not possible with fluorescein.

MLCT probes display lifetimes that range from subnanosecond to >100 $\mu s$. Therefore, MLCT compounds can be specifically tailored to be used in any immunoassay. MLCT compounds can be systematically engineered to alter their spectroscopic, photophysical, and chemical properties. The spectral and chemical versatility of MLCT complexes allows the design of probes displaying lifetimes that respond to specific molecular weights. Compared to $[Ru(bpy)_2(dcb)]^{2+}$, $[Re(bcp)(CO)_3(4\text{-}COOHPy)]^+$ displays higher quantum yield, higher anisotropy, and longer lifetime. The quantum yields of $[Ru(bpy)_2(dcb)]^{2+}$ and $[Re(bcp)(CO)_3(4\text{-}COOHPy)]^+$ are about 0.05 and 0.12, respectively, when bound to protein.

The invention is applicable to anisotropy probes for protein hydrodynamics.

The newly made Re-complex, $[Re(bcp)(CO)_3(4\text{-}COOHPy)](ClO_4)$, can be used as an anisotropy probe for protein hydrodynamics. $[Re(bcp)(CO)_3(4\text{-}COOHPy)]^+$ displays highly polarized emission with a maximal anisotropy near 0.3 in frozen solution, thus making it useful as an anisotropy probe. $[Re(bcp)(CO)_3(4\text{-}COOHPy)]^+$ was conjugated to human serum albumin (HSA) and bovine immunoglobin G (IgG). Long excited-state lifetimes in fluid solutions equilibrated with air at room temperature were found for $[Re(bcp)(CO)_3(4\text{-}COOHPy)]^+$ when covalently linked to HSA and IgG. Analyses of the anisotropy decays of the protein conjugates demonstrate that $[Re(bcp)(CO)_3(4\text{-}COOHPy)]^+$ can be used to measure rotational motions on the 10 ns to ~100 $\mu s$ timescale in air equilibrated solutions.

$[Re(bcp)(CO)_3(4\text{-}COOHPy)]^+$ can be used as an anisotropy probe for macromolecular dynamics. The anisotropy decays are dependent on protein dynamics. The correlation time has been extended to 100 $\mu s$, which has been inaccessible with routinely used nanosecond probes. This metal-ligand complex, with its high quantum yield, long lifetime, and highly polarized emission has opened a new timescale regime for the study of macromolecular dynamics.

The usefulness of the fluorescence anisotropy measurements is derived from its dependence on the extent of rotational diffusion during the lifetime of the excited state. Two basic kinds of information may be derived from fluorescence anisotropy decay measurements. Anisotropy decay may provide information as to the size and shape factor of macromolecules, reflecting the macromolecule and the attached fluorophore which rotate as a unit. Anisotropy decays may also provide information about the internal rotational motions present in the macromolecules and the nature of the molecular flexibility. Information about the rotational motion is available over a time range extending to about 3 times the fluorescence lifetime, after which there is too little signal for accurate anisotropy measurements. Because the lifetime of typical fluorophores ranges from 1 to 10 ns, it is difficult to measure rotation correlation times larger than 30 ns. Therefore, it is difficult to determine the rotational hydrodynamics of larger proteins or membrane-bound proteins.

The invention also is applicable to red fluorescent dyes for biophysics and for sensors.

Several polypyridine compounds of osmium(II) have been synthesized. These compounds can be conjugatable to proteins, typically absorb above 550 nm, emit above 700 nm and their lifetimes are higher than 50 ns. The emission of these compounds is polarized, so they have excellent applications as LED excitable and red emitting dyes for biophysical experiments. The low energy absorption as well as emission and high lifetime can be used for lifetime based oxygen sensing.

We have developed rhenium and osmium metal ligand complexes which are very photostable, have polarized emission and long decay times. The longer decay times allow increased sensitivity using gated detection following decay of the unwanted autofluorescence. Some lanthanide chelates compounds show longer decay times which allow gated detection and increased sensitivity for immunoassays, but do not display polarized emission, which is required for protein hydrodynamics.

The dyes consist of MLCT complexes of osmium(II) metal with polypyridine and nonchromophoric tridentate phosphine ligands. FIG. 17 represents the structure of all ligands used, and FIG. 10 represents the structure of two complexes of each class. All these complexes show good fundamental anisotropy ($r_0$) and long decay times. Therefore, they can be used in biophysics to study the hydrodynamics of macromolecules. Another added advantage of using these complexes is their high photo-stability in solvents.

Figure 14:
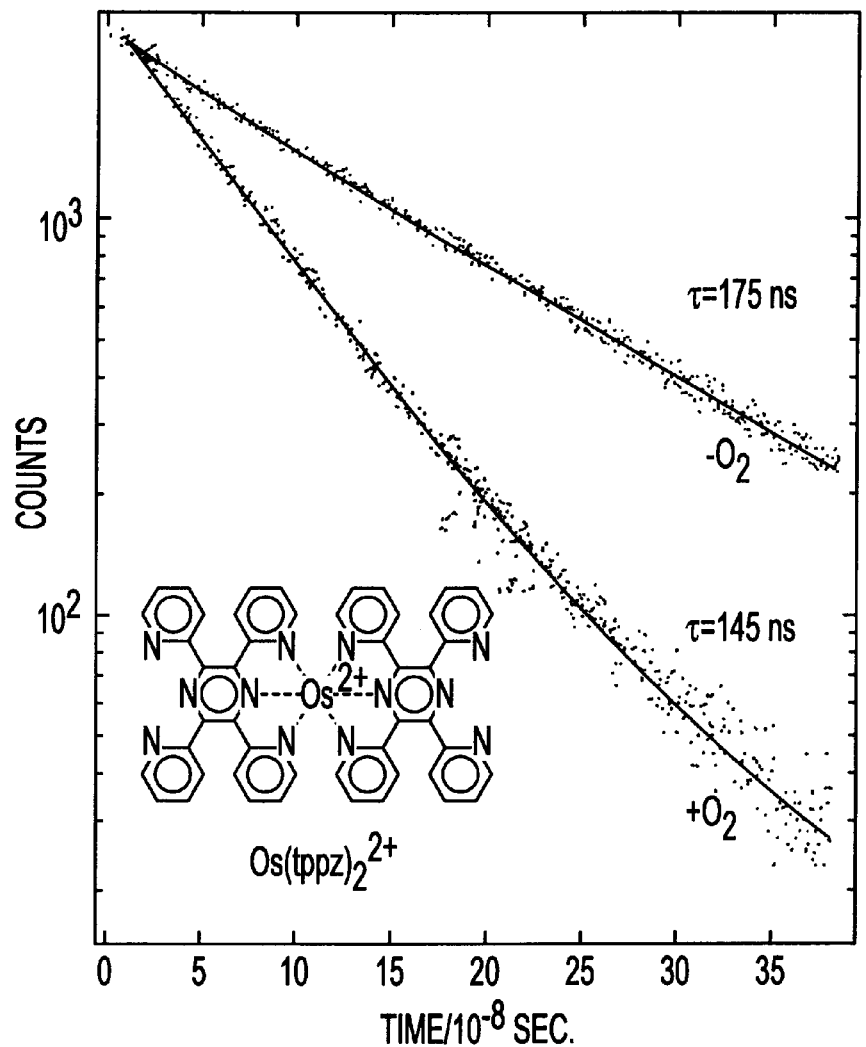
FIG. 14 graphically depicts the intensity decay of long lifetime $[Os(tppz)_2]^{2+}$.
Figure 15:
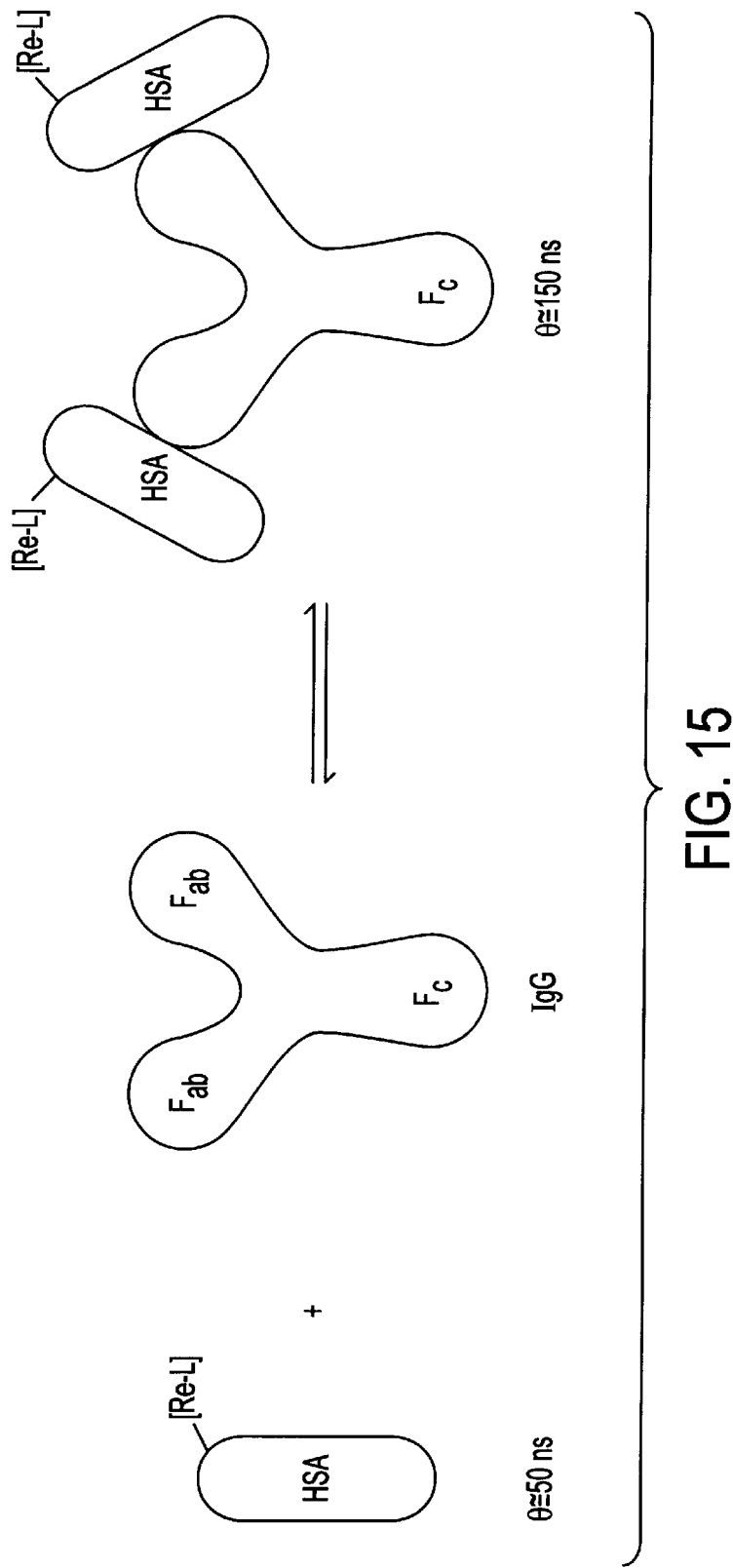
FIG. 15 is an intuitive description of a fluorescence polarization immunoassay. Re-L is $[Re(bcp)(CO)_3(4\text{-}COOHPy)]^+$, and θ is the rotational correlation time.

The long lifetimes of rhenium (I), ruthenium (II) and osmium (II) complexes allow their use as oxygen sensors. The effect of oxygen on osmium complexes is less than its effect on the analogous ruthenium complexes because of shorter excited state lifetimes. The lifetime of these complexes is long enough to use them as oxygen sensors for lifetime based sensing using low-cost phase fluorometry with red emitting, LED light sources. The effect of oxygen on $[Os(tppz)_2]^{2+}$ is represented in FIG. 14.

Because of their long decay lifetimes, diode laser excitability (absorb at 500–700 nm), low energy emission (emit in red region, 700–750 nm), reasonable quantum yields, polarized emission (anisotropy 0.15–0.35) and high photostability, these osmium(II) polpyridine complexes can be used as fluorophores in biophysical applications. These complexes can be used as red fluorophores for macromolecules. When using these fluorophores, one can avoid low signal to noise level by using gated observation. Another advantage of these compounds is high photostability. These dyes can be handled in room light for months.

These metal ligand complexes can be prepared with different functional groups for conjugation to biological macromolecules. These include isothiocyanate, sulfonyl chlorides, iodoacetamides, and malimides. Also, the organic ligands bound to the rhenium and osmium atoms can be varied to further modify the absorption and emission spectral properties.

The invention is further illustrated by the following examples, which are not intended to be limiting.

EXAMPLE 1

A Long-Lived, Highly Luminescent Rhenium (I) Metal-Ligand Complex as a Biomolecular Probe Human serum albumin (HSA), bovine immunoglobulin G (IgG), dipalmitoyl-L-α-phosphatidylethanolamine (PE) and dipalmitoyl-L-α-phosphatidylglycerol (DPPG) were obtained from Sigma Chemical Co. and were used without further purification. 2,9-dimethyl-4,7-diphenyl-1,10-phenanthroline (bcp), isonicotinic acid (4-COOHPy), $AgClO_4$, $NH_4PF_6$, and $Re(CO)_5Cl$ were obtained from Aldrich and used as received. The other solvents used were of HPLC or spectroscopic reagent grade. FTIR spectra were obtained on a Perkin Elmer 1600 Series spectrophotometer with 4 cm−1 resolution. Samples were dissolved in dichloromethane and measured in a liquid cell.

$Re(bcp)(CO_2)_3Cl$ Synthesis $Re(CO)_5Cl$ (1 g, 2.76 mmol) was reacted with bcp(1.05 g, 2.9 mmol) in toluene under reflux with stirring for 1 hour. The solution was cooled to room temperature and hexane was added which precipitated a yellow solid. This was collected on a coarse frit and washed with toluene followed by hexane. The product was dried under vacuum. Yield: 1.52 g (83%). Anal. Calcd for $ReC_{29}H_{20}N_2O_3Cl$: C, 52.29; H, 3.03; N, 4.21. Found: C, 52.04; H, 2.93; N, 3.95. IR (νCO: 2021(vs), 1914(vs), 1895(vs) cm$^{-1}$).

$Re(bcp)(CO_3)(PyCOOH)$ Synthesis $Re(bcp)(CO)_3Cl$ (1.5 g, 2.25 mmol), $AgClO_4$ (514 mgs, 2.48 mmol), and 4-COOHPy (8.3 g, 67.5 mmol) were refluxed in 4:1 MeOH:toluene under argon in the dark for 24 hours. This was cooled to room temperature and filtered to remove the AgCl precipitate. The filtrate was rotovaped to dryness and the solid resuspended in $CH_2Cl_2$ and filtered (to remove 4-COOHPy). The filtrate was rotovaped to dryness and a bright yellow solid was obtained. Yield: 1.8 g (94 %). Anal. Calcd for $ReC_{35}H_{25}N_3O_9Cl$: C, 49.27; H, 2.95; N, 4.92. Found: C, 50.30; H, 2.98; N, 4.80. IR (νCO: 2034(vs), 2022(vs), 1919(vs) cm$^{-1}$). FAB-MS [M-$ClO_4^-$]:755. The hexafluorophosphate salt was prepared by methathesis of the perchlorate salt by dissolving it in 1:1 acetone:$H_2O$ and precipitating it by the addition of a concentrated aqueous solution of $NH_4PF_6$. High purity luminescence samples were prepared using chromatography procedures previously described in the literature. (Wallace, L., and Rillema, D. P. (1993) *Inorg. Chem.* 32, 3836–3843;

Sacksteder, L., Zipp, A. P., Brown, E. A., Streich, J. Demas, J. N., and DeGraff, B. A. (1990) *Inorg. Chem.* 29, 4335–4340).

Preparation of Activated Succimidyl Ester 5 mg of N,N'-dicyclohexylcarbodiimide (DCC) and 3 mg of N-hydroxy-succinimide (NHS) were dissolved in 0.15 ml of DMF with stirring, 10 mg of the Re-complex in 0.15 ml of DMF was then added, and the mixture was stirred for a few hours. The formed precipitate was removed by filtration through a syringe filter, and the filtrate containing the active Re-complex was used for labeling the substrates.

The proteins HSA and IgG (10 mg of protein) were labeled by adding a 15-fold molar excess of the Re-NHS in 50 μl of DMF to 1 ml of stirred protein solution (0.2 M carbonate buffer, pH 8.5), followed by a 5 h incubation and purification of the labeled protein by gel filtration chromatography on Sephadex G-25, using 0.1 M PBS, pH 7.0. Our 0.1 M PBS (phosphate buffered saline) consisted of 0.1 M $NaH_2PO_4$ and 0.1 M $NaHPO_4$ in deionized water. The dye:protein ratio of the Re-HSA conjugate was determined to be 2:1. The concentration of the protein was determined by the Coomassie Plus Protein Assay (Pierce) and the concentration of the Re(I) complex was determined by its absorbance at 400 nm (e=5040 $M^{-1}cm^{-1}$), assuming the same extinction coefficient as the free complex.

95 mg of the Re-complex and 13 mg of NHS were dissolved in 0.7 ml of $CHCl_3$ at room temperature, 24 mg of DCC was then added. The mixture was sealed and stirred for a few hours. The formed precipitate was removed by filtration through a syringe filter, and the filtrate containing the active Re-complex was slowly added to a stirred solution of PE (60 mg in 7.5 ml of $CHCl_3$) and triethylamine (4.5 ml) under an argon atmosphere. The mixture was stirred for 20 h in the dark. The solvents were removed under vacuum and the product was redissolved in 1.0 ml of $CHCl_3$/MeOH (1/1,v/v). The pure Re-PE was obtained by TLC on K6F silica gel plates using $CHCl_3/CH_3OH/NH_3OH$ (65/25/4, v/v/v) as the developing solvent. The $R_f$ value of the product is about 0.91, relative to that of PE (0.55).

For vesicle preparation, lipids with a Re-lipid/DPPG mole ratio of 1:200 were dissolved in $CHCl_3$ and the solvent was removed by a stream of argon. Vesicles were prepared by sonicating in 10 mM Tris, 50 mM KCl, pH 7.5, at a final lipid concentration of 2 mg/ml of DPPG. The DPPG vesicles in the absence of Re-lipid did not display significant emission signals (<2%) under the present experimental conditions. Before sonication, the lipid and Re-complex were vacuum dessicated overnight to remove any traces of organic solvent. The vesicle solutions were deoxygenated by bubbling argon for 20 minutes, followed by equilibration with an argon atmosphere for 20 minutes, and then a subsequent 20 minute bubbling of the solution with argon.

Emission spectra were recorded on a SLM AB-2 spectrofluorimeter. The frequency-domain instrumentation (ISS) was used for measurements of luminescence intensity decays. The frequency-domain lifetime measurements of the free dye in solution were performed on an ISS (Champaign, IL) K2 fluorimeter, using a Panasonic high intensity blue LED (light-emitting diode) configured to provide amplitude modulated light centered at 390 nm. (Sipior, J., Carter, G. M., Lakowicz, J. R., and Rao, G. (1997) *Rev. Sci. Instrum.* 68(7), 2666–2670). An Andover (Salem, N.H.) 500 nm long-wave pass filter (500FH90-50S) was used to isolate the emission. For DPPG vesicle samples, frequency-domain lifetime measurements were performed using a Xenon arc lamp (300W) as the light source. The excitation was amplitude modulated by an electro-optical low-frequency modulator (K2.LF from ISS) using 340±8 nm as the excitation wavelength. A 470 nm long-pass filter (Corning 3-71) was used to isolate the emission.

The frequency-domain intensity data were fitted by a nonlinear least squares procedure and were modeled with single and multi-exponential decay laws. The intensity decays were described by $$I(t) = \sum_i \alpha_i e^{-t/\tau_i} \qquad (9)$$

where I(t) is the luminescence intensity at time t, $\alpha_i$ and $t_i$ are the pre-exponential weighting factors and the excited-state lifetimes, respectively. The subscripts denote individual components. Mean lifetimes were calculated using Equation 9.

$$\langle \tau \rangle = \sum_i \alpha_i \tau_i^2 \Big/ \sum_i \alpha_i \tau_i \qquad (10)$$

The measured excitation anisotropy spectra are defined by Equation 5, where $I_\parallel$ and $I_\perp$ are the emission intensities measured with vertically polarized excitation and the emission polarization parallel ($I_\parallel$) or perpendicular ($I_\perp$) to the excitation. The values of the polarized intensities were corrected for the transmission efficiency of the polarized components by the detection optics.

As a probe of emission heterogeneity, the excitation spectra method described by Demas and co-workers (Sacksteder, L., Demas, J. N., and DeGraff, B. A. (1989) *Inorg. Chem.* 28, 1787–1792) was used. In brief, two uncorrected excitation spectra were measured with different emission wavelengths ($\lambda_1$ and $\lambda_2$). R ($\lambda$) is calculated as $$R(\lambda) = E_1(\lambda)/E_2(\lambda) \qquad (11)$$

where the E's are the emission intensities while exciting at $\lambda$ and monitoring at two different wavelengths, $\lambda_1$ and $\lambda_2$. Since the sample absorbance and excitation intensities are the same at each excitation wavelength, R is related to the relative contributions of different emission components. If there is no ground-state heterogeneity or the equilibration in the excited state is rapid relative to sample decay times, R ($\lambda$) is wavelength independent. If there are multiple ground-state species that fail to equilibrate in their excited states, R ($\lambda$) varies with $\lambda$.

Figure 18:
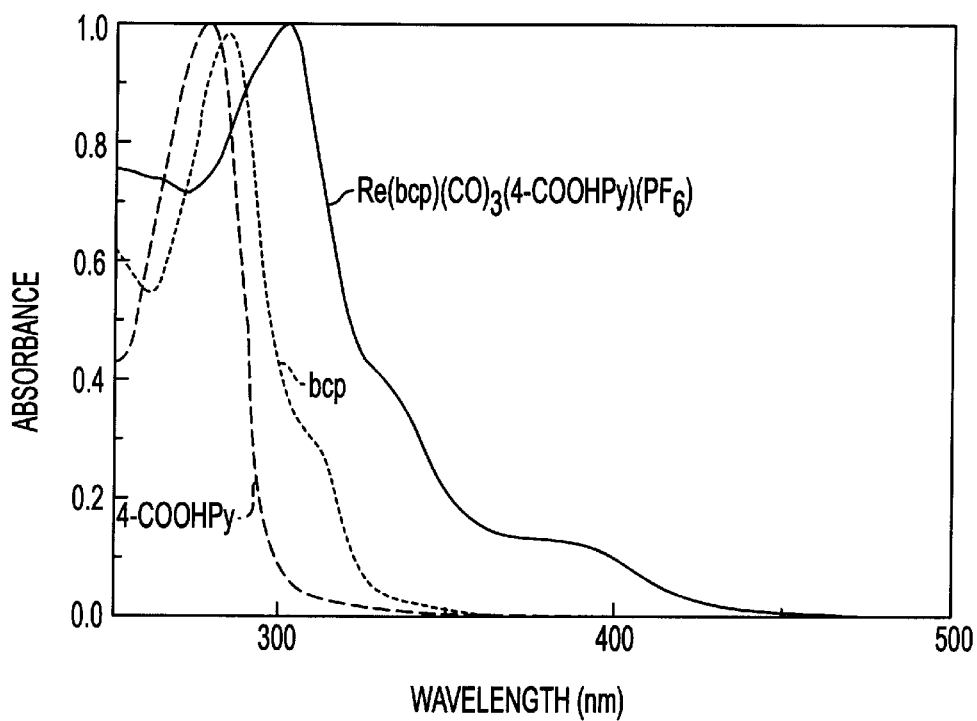
FIG. 18 graphically depicts the absorption spectra of $[Re(bcp)(CO)_3(4\text{-}COOHPy)]^+$, 2,9-dimethyl-4,7-diphenyl- 1,10-phenanthroline (bcp), and isonicotinic acid (4-COOHPy) in methanol.

The molecular structure of [Re(bcp)(CO)$_3$(4-COOHPy)]$^+$ is shown in FIG. 1. The absorption spectrum of the Re-complex in CH$_3$OH is shown in FIG. 18. The absorption spectra of the ligands in CH$_3$OH are also shown for comparison. The spectra are normalized to unity to facilitate comparison. The maximum of the low-energy absorption band around 340–450 nm and the more intense higher energy absorption at 298 nm are the characteristic MLCT and π—π* bands, respectively. It is important to note that this complex can be excited with the UV output of a blue light emitting diode.

Figure 2:
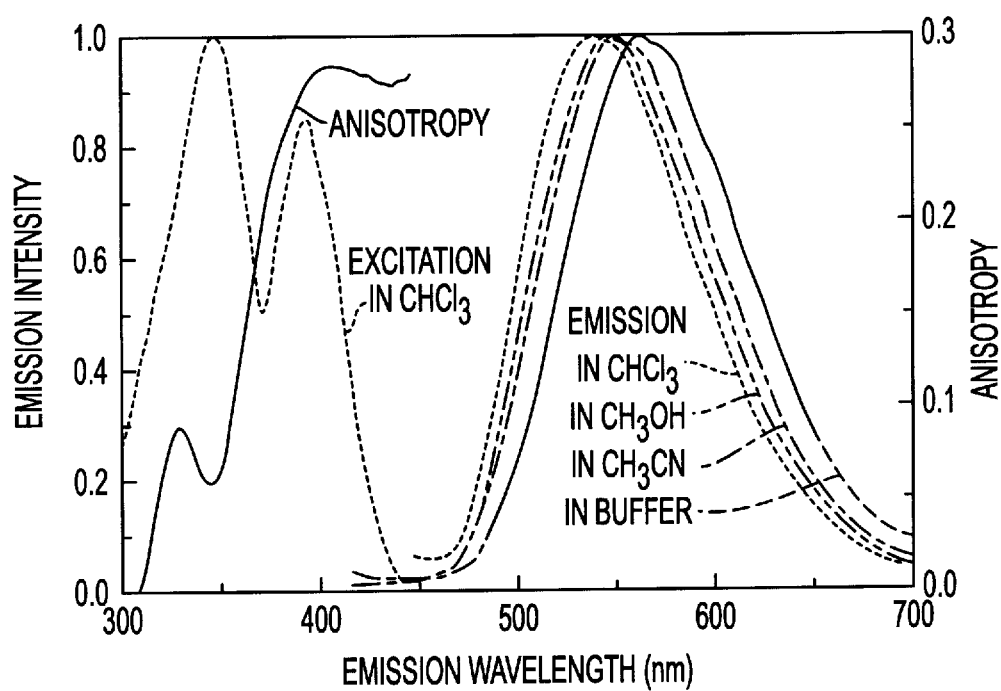
FIG. 2 is a graph depicting the absorption and emission spectra of $[Re(bcp)(CO)_3(4\text{-}COOHPy)]^+$ in $CHCl_3$, $CH_3CN$, $CH_3OH$, and in buffer, at room temperature. The excitation wavelength was 400 nm. The solid line shows the excitation anisotropy spectrum in 100% glycerol at −60° C., with the emission wavelength tuned to 550 nm. The bandpass was 8 nm for all measurements.
Figure 19A:
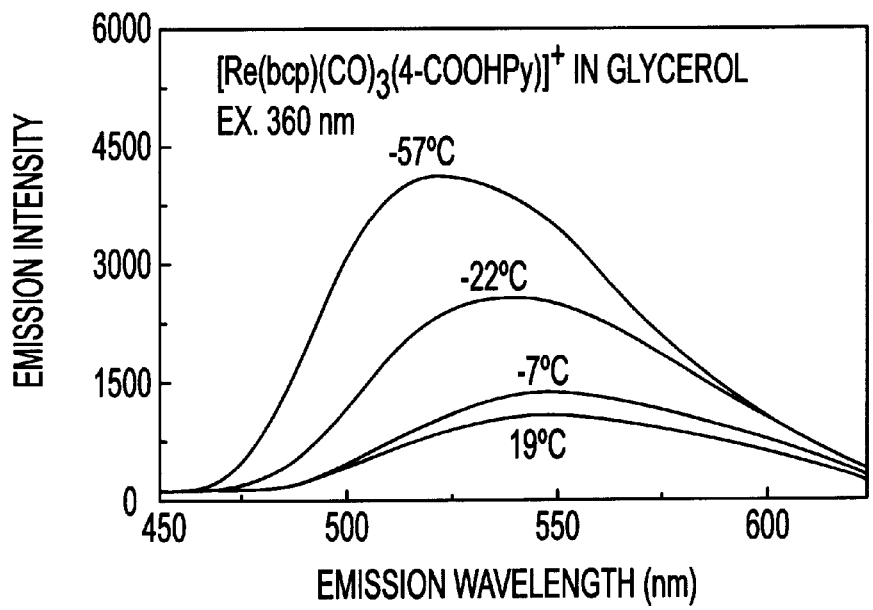
FIG. 19 graphically shows the temperature dependent emission spectra (top) and intensity-normalized emission spectra (bottom) of [Re(bcp)(CO)$_3$(4-COOHPy)]$^+$ in 100% glycerol. Excitation was 360 nm with a bandpass of 8 nm.
Figure 19B:
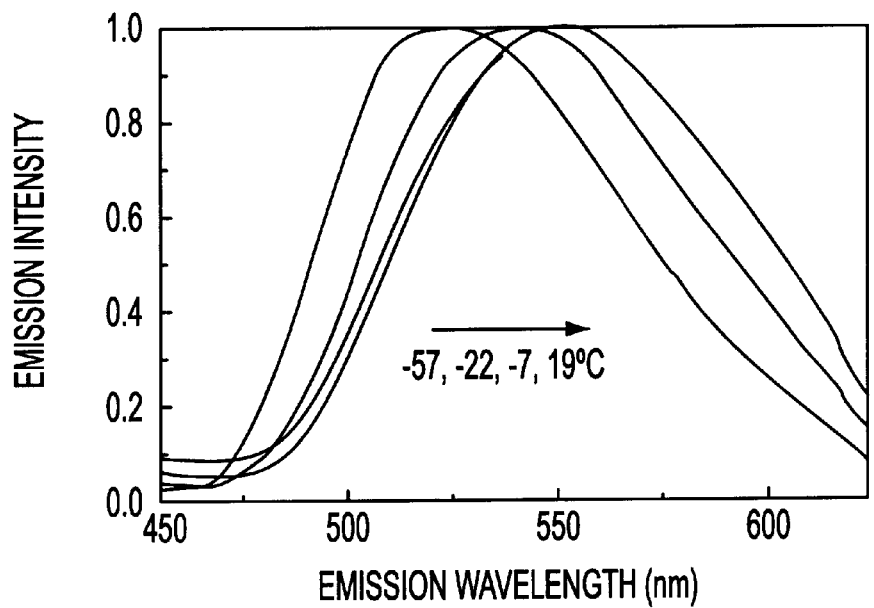

The excitation and emission spectra of the Re complex in CHCl$_3$, CH$_3$OH and CH$_3$CN are shown in FIG. 2. The large Stokes' shift of this Re complex (~100 nm) makes it a good candidate for energy transfer studies as there is no possibility for self-quenching. Also, the large Stokes' shift indicates a macromolecule can be labeled with multiple MLCT without self-quenching. This emission of this complex displays a strong sensitivity to local environment, as observed from the spectral shift of 539 nm in CHCl$_3$ to 559 nm in 0.1 M PBS buffer solution at room temperature. When bound to biomolecules it is reasonable to expect that this complex's emission may respond to the subtle changes in the microenvironment of a biological sample. The emission intensity is strongly dependent on temperature as shown by the increased intensity at –57° C. compared with 19° C. (FIG. 19). There is also a significant blue-shift in emission maximum with decreasing temperature (FIG. 19). These results are consistent with the temperature dependence of many other MLCT complexes, wherein the energy gap between the ground and excited states increases with decreasing temperature resulting in a blue-shifted emission spectrum, increased lifetime, and higher quantum yield.

The lifetimes and quantum yields for [Re(bcp)(CO)$_3$(4-COOHPy)]$^+$ are summarized in Table 1.

TABLE 1

Photoluminescence quantum yields and lifetimes of Re(bcp)(CO)$_3$(4-COOHPy)(PF$_6$) at room temperature unless otherwise indicated.

| Solvent | Conditions | φ$^a$ | τ(μs) | mean τ(μs) |
|---|---|---|---|---|
| CH$_3$OH | Air | 0.039 | 0.54 | |
| | Argon | 0.54 | 7.25 | |
| CHCl$_3$ | Air | 0.047 | 0.66 | |
| | Argon | 0.55 | 6.72 | |
| CH$_3$CN | Air | 0.016 | 0.49 | |
| | Argon | 0.23 | 4.65 | |
| Glycerol | Air | 0.27 | 10.8 | |
| Re-PE in DPPG vesicles | Air | 0.13 (22° C.) | | 4.36(2° C.) 3.31(10° C.) 2.54(22° C.) 1.99(35° C.) 1.82(50° C.) |
| | Argon | 0.27 | | |
| Re-IgG | Air | 0.12 | | 2.92 |
| | Argon | 0.22 | | 4.07 |
| Re-HSA | Air | 0.20 | | 2.75 |
| | Argon | | | 3.44 |
| 0.1 M PBS | Air | | 0.99 | |

$^a$Absolute quantum yields are difficult to determine in the presence of uncertain amounts of dissolved oxygen under air-equilibrated conditions.

Figure 3:
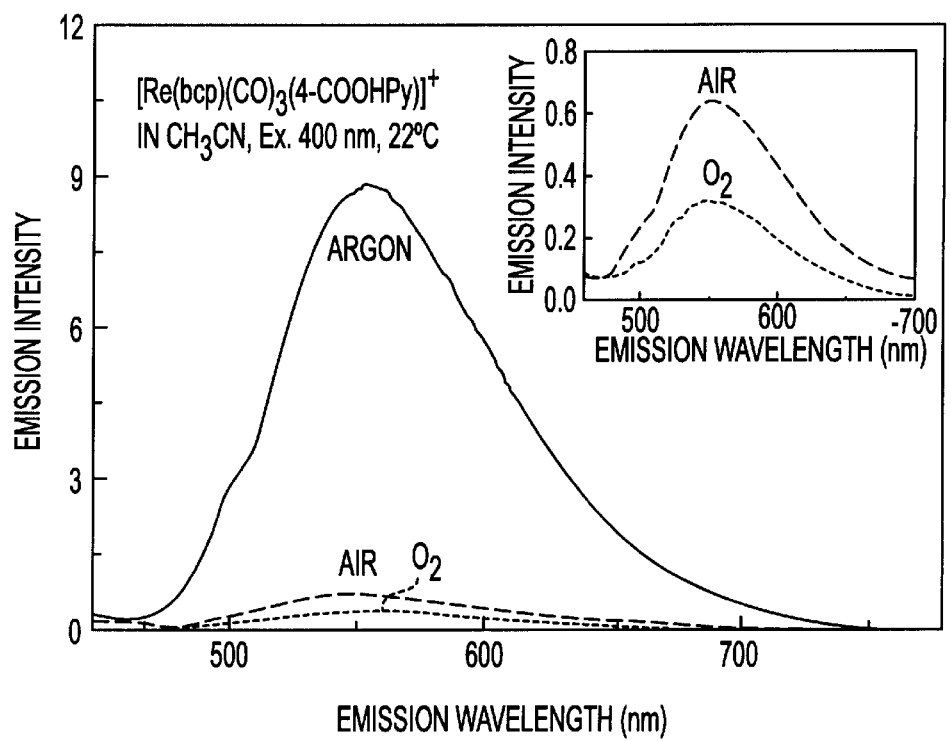
FIG. 3 graphically shows that in organic solutions, $[Re(bcp)(CO)_3(4\text{-}COOHPy)]^+$ is highly sensitive to dissolved oxygen, but in the absence of dissolved oxygen, it displays a lifetime over 7 μs. The oxygen dependent spectra of the rhenium complex was taken at room temperature, excitation was 400 nm, and with a bandpass of 8 nm. The inset shows spectra obtained in air and oxygen.
Figure 4:
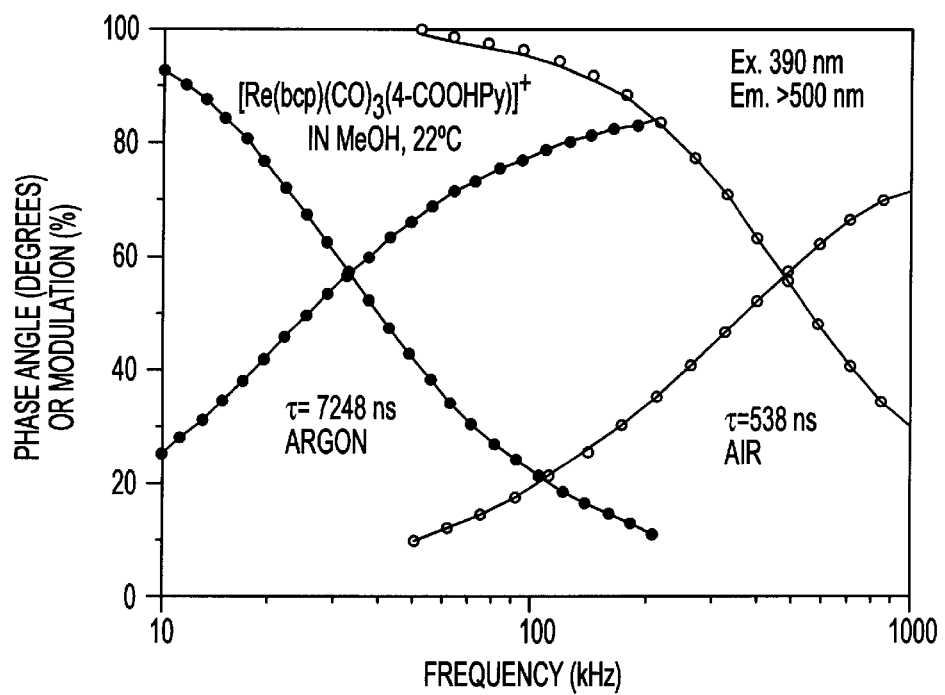
FIG. 4 graphically shows the frequency-domain intensity decays of $[Re(bcp)(CO)_3(4\text{-}COOHPy)]^+$ in methanol. The lifetime is reduced to about 0.5 microseconds in the presence of dissolved oxygen from the atmosphere. The excitation was 390 nm and a 500 nm cutoff filter was used to isolate the emission.
Figure 5:
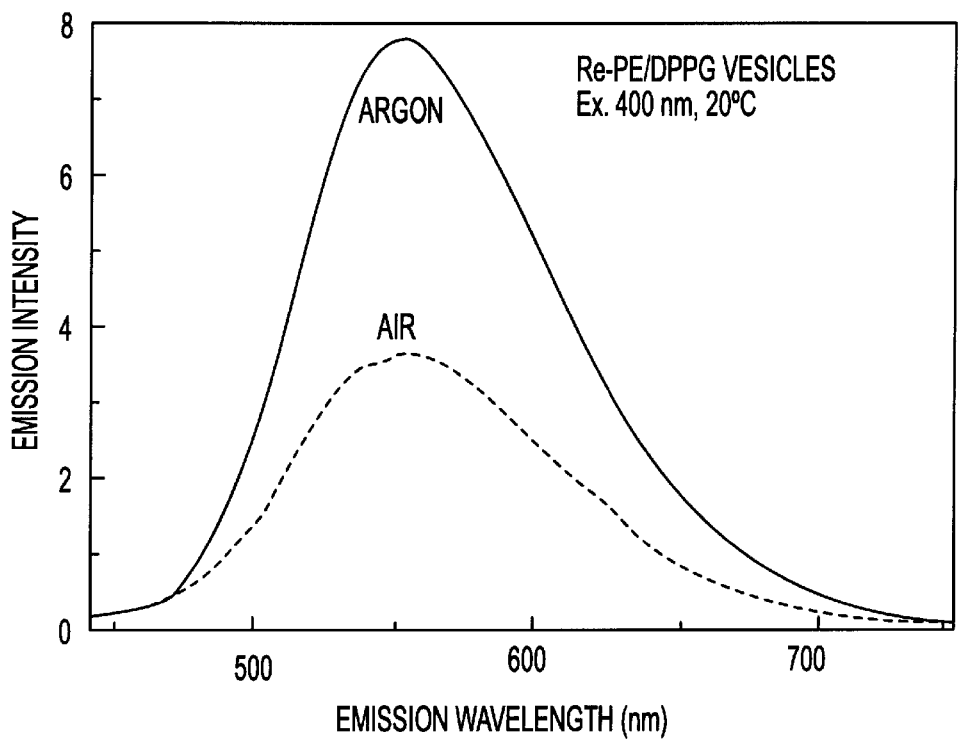
FIG. 5 graphically shows the emission spectra of $[Re(bcp)(CO)_3(4\text{-}COOHPy)]^+$ when conjugated to phosphatidyl ethanolamine and embedded into DPPG vesicles. The mole ratio of the rhenium complex to phosphatidyl ethanolamine was 1:80. The excitation was 400 nm with a bandpass of 8 nm, measured at 20° C.

Demas and co-workers have demonstrated that certain rhenium complexes display high quantum yields, in excess of 0.7, and long lifetimes in excess of 10 μs in fluid solutions at room temperature. (Sacksteder, L., Lee, M., Demas, J. N., and DeGraff, B. A. (1993) *J. Am. Chem. Soc.* 115, 8230–8238). Our novel Re(I) complex is a remarkable example of such a high quantum yield long lifetime probe. It displays a lifetime over 10 μs in air-equilibrated glycerol, and long lifetimes when the lipid conjugate Re-PE is embedded in DPPG model vesicles, as shown in Table 1. Owing to its long lifetime, it is also extremely sensitive to oxygen quenching. There is a significant increase in intensity with the removal of oxygen from the solution, as shown in FIG. 3. In methanol, in the absence of oxygen, a homogeneous intensity decay with a lifetime of 7248 ns was found. In the presence of dissolved oxygen, from equilibrium with air, the lifetime reduced to 538 ns (FIG. 4). This result suggests that this complex may be used as an oxygen sensor under certain circumstances. The oxygen quenching, however, is much less efficient when the probe is bound to macromolecules, such as phospholipid vesicles, than when free in solvents (FIG. 5). We attribute this to a shielding of the excited state from oxygen quenching by macromolecules. More importantly, this complex displays a lifetime of 2.54 $\mu$s and a quantum yield of 0.13 in DPPG vesicles in aqueous solution at 22° C., which indicates that this long-lived probe can be used in presence of dissolved oxygen and still display a long decay time and exhibit a high quantum yield.

Figure 20:
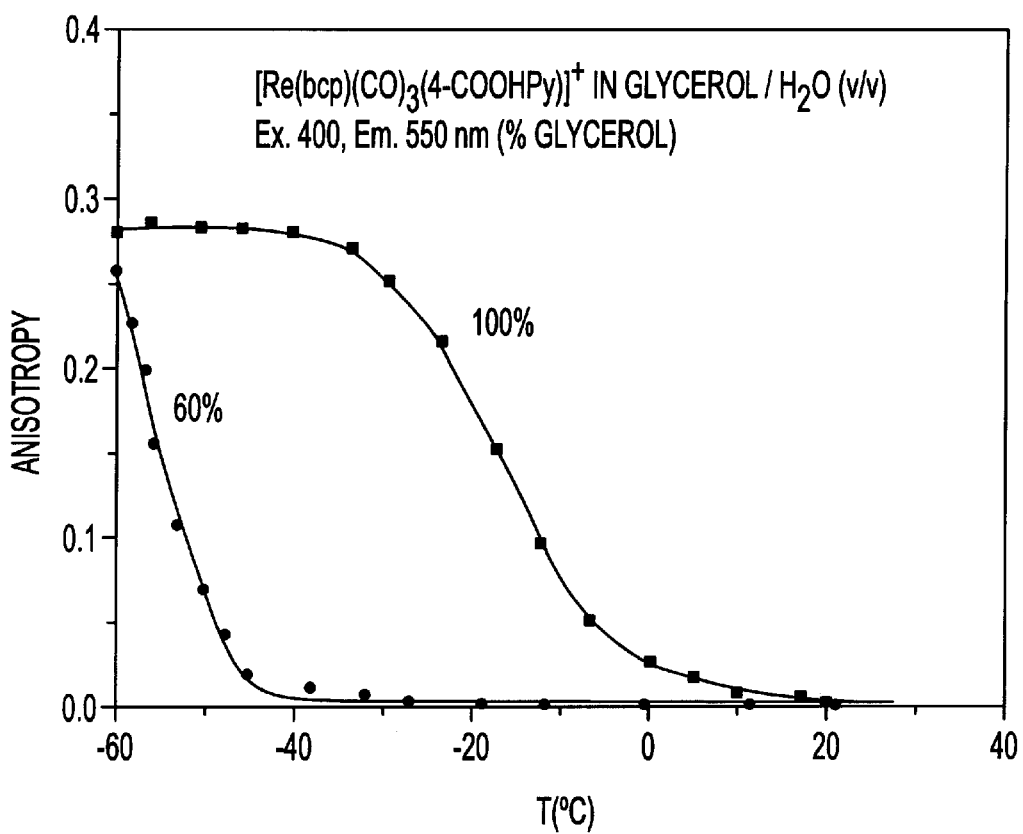
FIG. 20 depicts the temperature-dependent emission anisotropy of [Re(bcp)(CO)$_3$(4-COOHPy)]$^+$ in solutions composed of different ratios of glycerol/H$_2$O (v/v). Emission was monitored at 550 nm with an excitation wavelength of 400 nm and a bandpass of 8 nm.

We also studied the polarized emission of this complex in the absence of rotational diffusion (glycerol, −60° C.). The excitation anisotropy spectrum is shown in FIG. 2 which displays a maximum anisotropy near 0.3 from 390 nm to 450 nm. The anisotropy of this complex is also sensitive to solution viscosity, as shown in FIG. 20. FIG. 20 is not meant to yield an exact relationship between the anisotropy and solution viscosity. For example, at the same temperature, the viscosity of a 100% glycerol solution is larger than that of a 60% glycerol:water solution, and the anisotropy values demonstrate this behavior.

Figure 21:
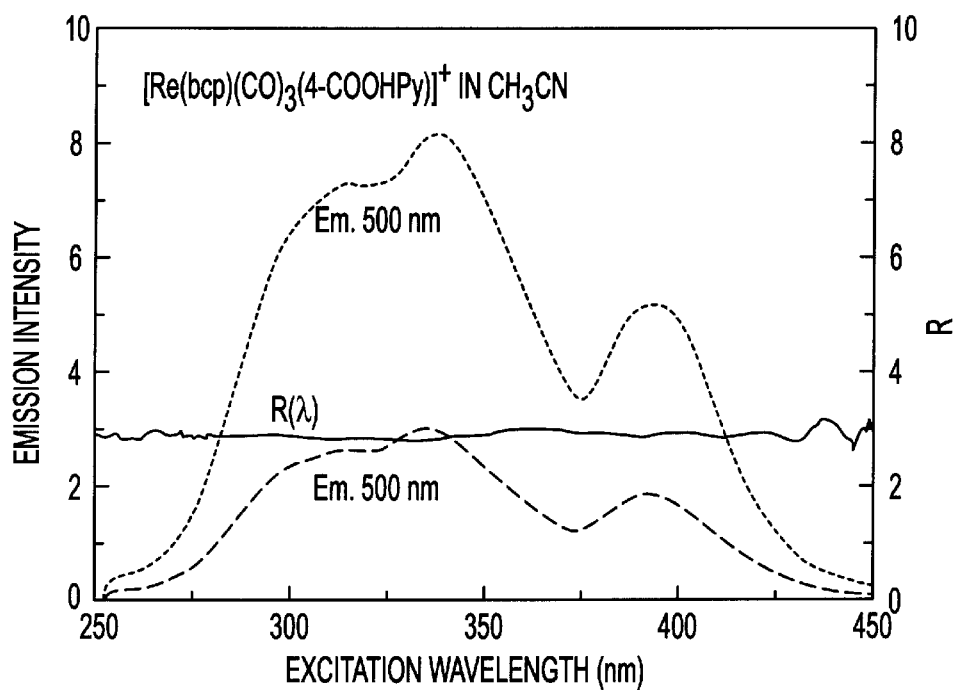
FIG. 21 graphically shows excitation spectra and R($\lambda$) values for [Re(bcp)(CO)$_3$(4-COOHPy)]$^+$ in CH$_3$CN.

Rhenium (I) complexes are known to display dual emission, which can originate from either a metal-to-ligand charge transfer state or a ligand-centered state (LC). The MLCT states typically show an unstructured emission whereas the LC states often display a structural emission which is characteristic of ligand. The emission spectra in FIG. 2 are unstructured, suggesting that under our experimental conditions the emission is from a pure MLCT state. The R($\lambda$) values are flat across the excitation spectrum, which suggests that regardless of excitation wavelength, only one excited state parentage is created (FIG. 21).

Figure 22:
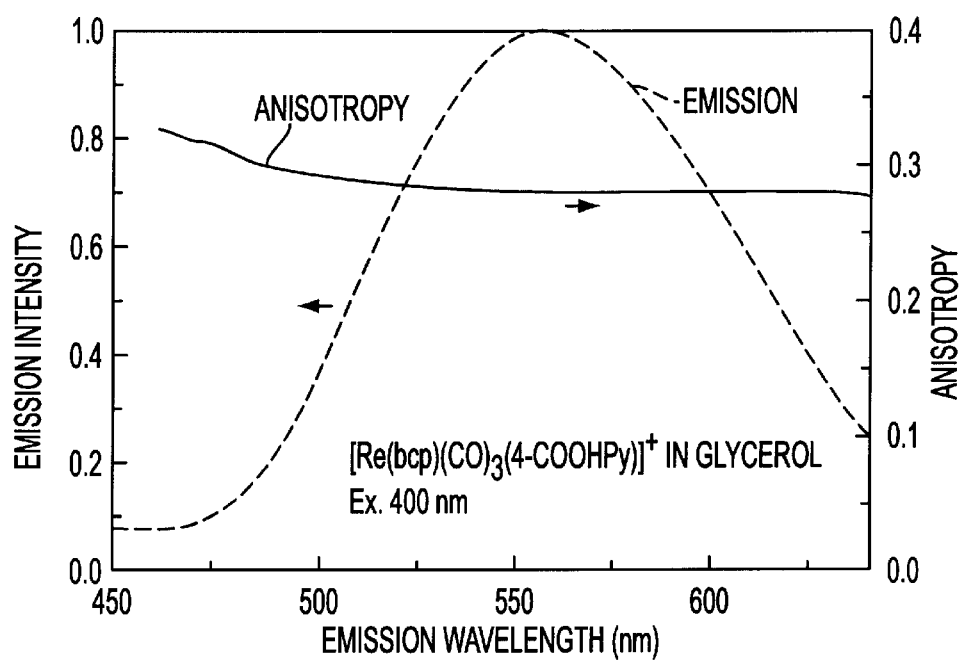
FIG. 22 depicts the emission anisotropy spectrum of [Re(bcp)(CO)$_3$(4-COOHPy)]$^+$ in 100% glycerol at −60° C. An emission spectrum is shown for comparison. Excitation was 400 nm with a bandpass of 8 nm.

To further clarify the nature of the emission, and to characterize this complex for use as biophysical probe, we examined the emission anisotropy (FIG. 22). The anisotropy is rather constant across the entire emission spectrum and displays a gradual decrease with increasing wavelength.

Figure 6:
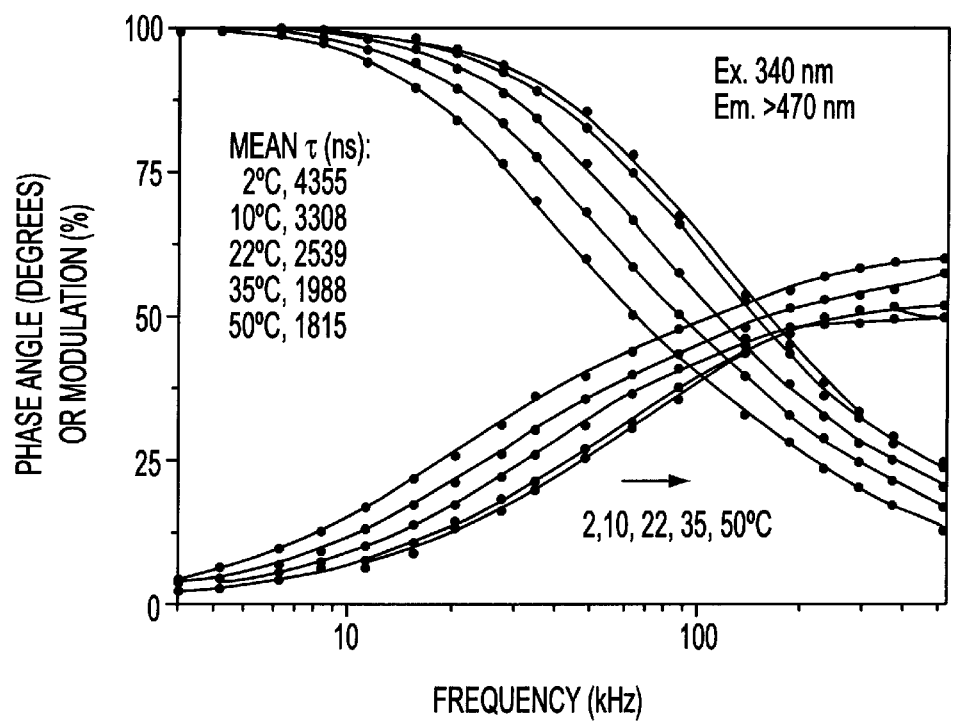
FIG. 6 graphically shows the lifetimes of $[Re(bcp)(CO)_3(4\text{-}COOHPy)]^+$ labeled DPPG vesicles measured by the frequency-domain or phase-modulation method. Excitation was 340 nm and a 470 nm cutoff filter was used to isolate the emission.

For use as a biomolecular probe, this complex was used to label the proteins bovine IgG and HSA, as well as the lipid PE. The lipid conjugate Re-PE was used to label the DPPG vesicles. The preliminary results demonstrate that this complex is conjugatable and that its water solubility is adequate for the usual labeling procedures used with the biomolecules. The typical frequency-domain intensity decays of DPPG vesicles labeled with Re-PE are shown in FIG. 6. The decays were best fit using three exponential components, along with a scattering component. The recovered long lifetimes when bound to proteins and lipid model vesicles indicate that this complex might be used to study protein and membrane hydrodynamics and measure rotational correlation times longer than 10 $\mu$s.

EXAMPLE 2
Fluorescence Polarization Immunoassays of High Molecular Weight Analytes Human serum albumin (HSA), human immunoglobulin G (IgG), and monoclonal IgG specific for HSA (anti-HSA) from mouse ascites were obtained from Sigma Chemical Co. and were used without further purification. All other reagents and all solvents used were reagent grade. The synthesis of [Re(bcp)(CO)$_3$(4-COOHPy)] (ClO$_4$) is described in Example 1.

5 mg of N,N'-dicyclohexylcarbodiimide (DCC) and 3 mg of N-hydroxy-succinimide (NHS) were dissolved in 0.15 mL of DMF with stirring. [Re(bcp)(CO)$_3$(4-COOHPy)] (ClO$_4$) (10 mg in 0.15 mL of DMF) was added, and the mixture was stirred for 20 hours. The formed precipitate was removed by filtration through a syringe. filter, and the filtrate containing the activated Re-complex was used for labeling the substrates.

The protein HSA (10 mg) was labeled by adding a 15-fold molar excess of the activated Re-complex in 50 $\mu$l of DMF to 1 mL of stirring protein solution (0.2 M carbonate buffer, pH 8.5), followed by a 5 hr incubation. The conjugate was purified by gel filtration chromatography on Sephadex G-25, using 0.1 M PBS, pH 7.0 as eluent. The dye:protein ratio of the Re-HSA conjugate was determined to be 2:1. The concentration of the protein was determined by the Coomassie Plus Protein Assay. The concentration of the Re(I) complex was determined by its absorbance at 400 nm, assuming the extinction coefficient was the same as that of the free dye ($\epsilon_{400}$=5040 M$^{-1}$cm$^{-1}$). (Guo, S. Q., Li, L., Castellano, F. N., Szmacinski, H., Lakowicz, J. R. *Anal. Biochem.* submitted). The equilibrium association constants of the bioconjugates were determined from luminescence anisotropy data as described in the literature. (Dandliker, W. B., Kelly, R. J., Dandliker, J., Farquhar, J., Levin, J. *Immunochemistry* 1973, 10, 219–227).

Uncorrected emission spectra were recorded on a SLM AB2 Spectrofluorimeter. The frequency-domain lifetime measurements were performed on an ISS K2 fluorimeter, using a high intensity Panasonic blue LED (light-emitting diode) configured to provide amplitude modulated light centered at 390 nm. (Guo, X. Q., Li, L., Castellano, F. N., Szmacinski, H., Lakowicz, J. R. *Anal. Biochem.* Submitted; Sipior, J., Carter, G. M., Lakowicz, J. R., Rao, G. *Rev. Sci. Instrum.* 1997, 68(7), 1–5). An Andover 500 nm long pass filter (500FH90-50S) was used to isolate the emission.

The frequency-domain intensity decay data were fit by a nonlinear least squares procedure, generally to a sum of three single-exponential decays. The intensity decays were described by Equation 9. Mean lifetimes were calculated using Equation 10.

The excitation anisotropy spectrum is defined by Equation 5, where $I_\parallel$ and $I_\perp$ are the emission intensities measured with vertically polarized excitation and the emission polarization parallel ($I_\parallel$) or perpendicular ($I_\perp$) to the excitation. The values of the polarized intensities were corrected for the transmission efficiency of the polarized components by the detection optics.

Figure 23:
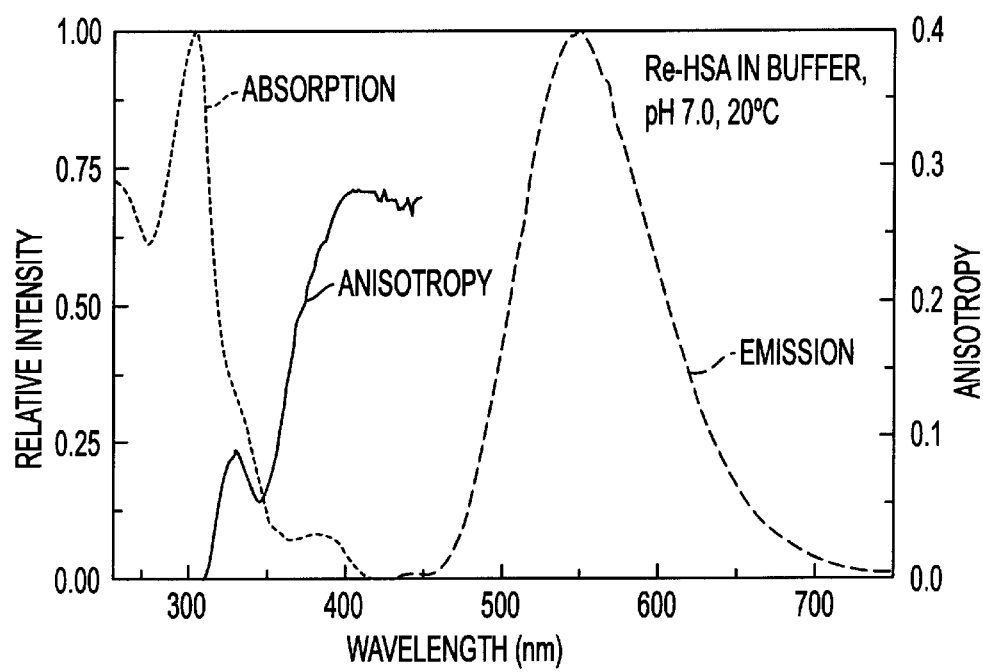
FIG. 23 graphically shows the absorption and emission spectra of [Re(bcp)(CO)$_3$(4-COOHPy)]$^+$ conjugated to HSA in 0.1 M PBS buffer, pH 7.0. Excitation wavelength was 400 nm. The solid line shows the excitation anisotropy spectrum in 100% glycerol at −60° C., with an emission wavelength of 550 nm. The bandpass was 8 nm for all measurements.

The molecular structure of [Re(bcp)(CO)$_3$(4-COOHPy)]$^+$ is shown in FIG. 1. The absorption and emission spectra of [Re(bcp)(CO)$_3$(4-COOHPy)]$^+$ labeled to HSA are shown in FIG. 23. The spectra are normalized to unity for comparative purposes. The absorption profile in the low-energy region (340–425 nm) and the more intense higher energy band at 290 nm are characteristic metal-to-ligand charge transfer and $\pi$—$\pi$* transitions, respectively. The emission spectrum is broad and has a maximum near 550 nm. These photophysical characteristics are similar to that observed with the parent complex [Re(bcp)(CO)$_3$(Py)]$^+$, where Py is pyridine. (Zipp, A. P., Sacksteder, L. A., Streich, J., Cook, A., Demas, J. N., DeGraff, B. A. *Inorg. Chem.* 1993, 32, 5629–5632). The large Stokes' shift of MLCT complexes in general can be exploited in biological media where multiple labeling of close proximity residues will not result in self-quenching processes.

Figure 7:
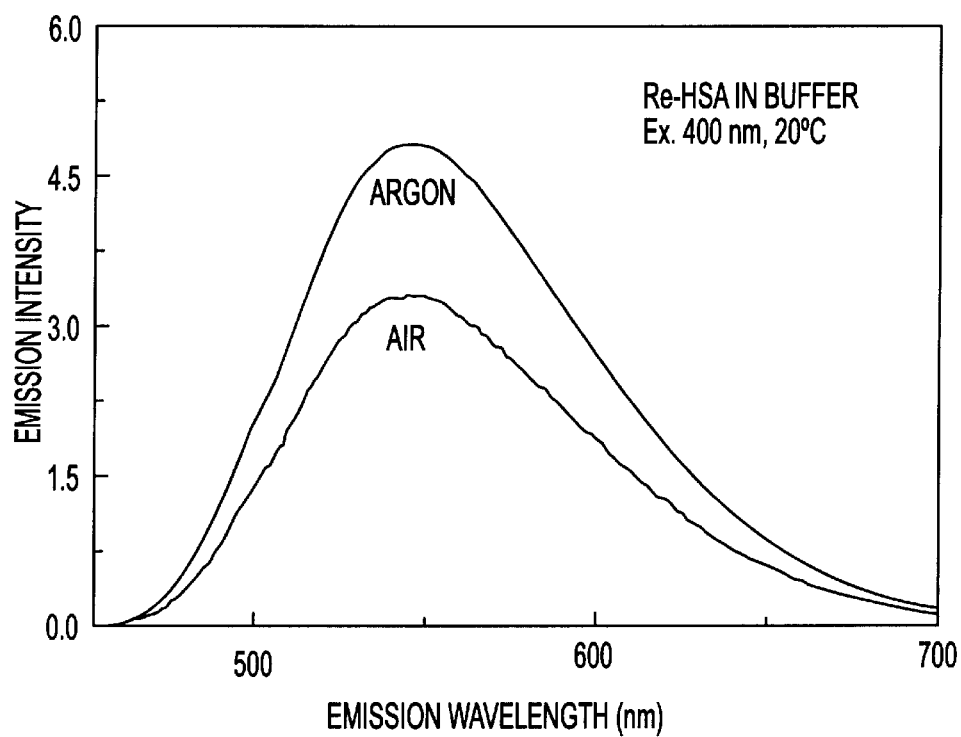
FIG. 7 graphically shows that similar favorable properties were found for $[Re(bcp)(CO)_3(4\text{-}COOHPy)]^+$ when conjugated to human serum albumin (HSA). The rhenium complex was conjugated to HSA in 0.1 M PBS buffer, pH 7.0, and equilibrated with argon or air. The excitation wavelength was 400 nm with a bandpass of 8 nm, at 20° C.

O₂ quenching is commonplace from MLCT excited states of Re(I) complexes. (Guo, X. Q., Li, L., Castellano, F. N., Szmacinski, H., Lakowicz, J. R. *Anal. Biochem.* Submitted; Sacksteder, L. A., Zipp, A. P., Brown, E. A., Streich, J., Demas, J. N., DeGraff, B. A. *Inorg. Chem.* 1990, 29, 4335–4340; Zipp, A. P., Sacksteder, L. A., Streich, J., Cook, A., Demas, J. N., DeGraff, B. A. *Inorg. Chem.* 1993, 32, 5629–5632). In the case of [Re(bcp)(CO)$_3$(4-COOHPy)]$^+$, the oxygen quenching is modest when the probe is bound to HSA in air-equilibrated aqueous solution. Compared to a deoxygenated buffer solution (1.0), the relative photoluminescence intensity of Re-HSA in air-equilibrated buffer solution is 0.69 (FIG. 7).

We examined the steady-state excitation anisotropy spectrum of [Re(bcp)(CO)$_3$(4-COOHPy)]$^+$ in vitrified solution (glycerol, −60° C.) where rotational diffusion does not occur during the excited state lifetime (FIG. 23). This complex shows a maximum anisotropy near 0.3, whose values are constant from 390 nm to 450 nm.

Figure 8:
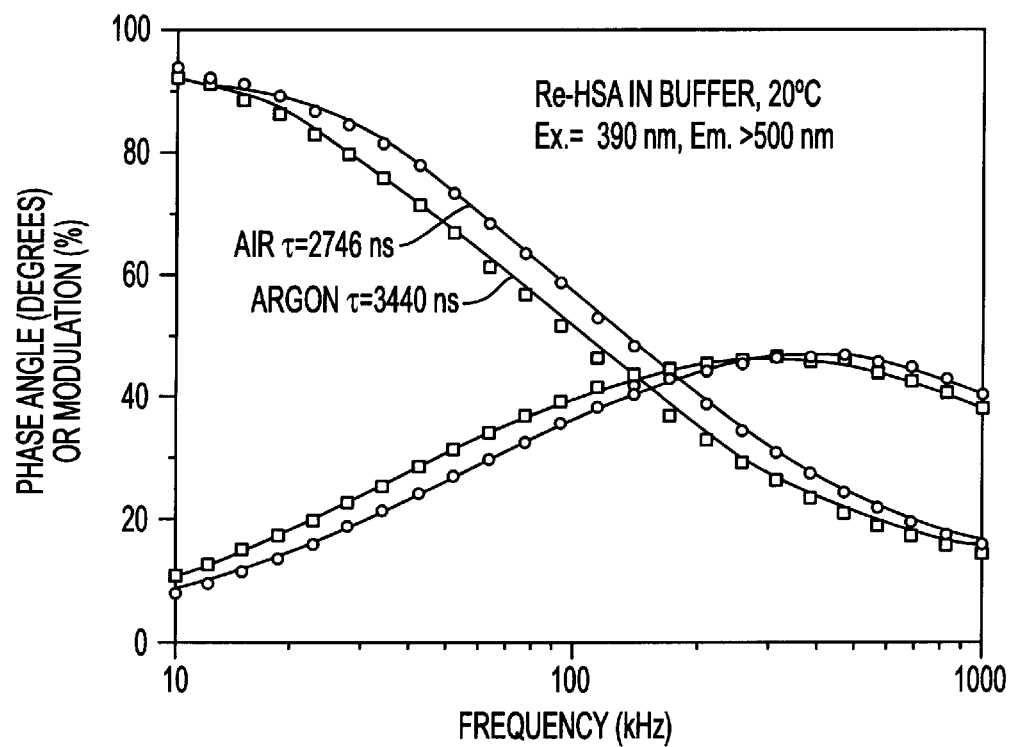
FIG. 8 graphically shows that the lifetime of $[Re(bcp)(CO)_3(4\text{-}COOHPy)]^+$ when conjugated to HSA is near 3 μs in the presence or absence of dissolved oxygen from the atmosphere. The excitation was 390 nm and a 500 nm cutoff filter was used to isolate the emission.

Frequency-domain intensity decays of Re-HSA in air-equilibrated and argon-equilibrated 0.1 M PBS buffer solutions are shown in FIG. 8. The analysis of the frequency-domain intensity decays are summarized in Table 2.

TABLE 2

Recovered intensity decays parameters of [Re(bcp)(CO)$_3$(4-COOHPy)]$^+$ conjugated to HSA.

|  | Condition | $\tau_i(\mu s)$ | $\alpha_i$ | Mean $\tau(\mu s)$ |
|---|---|---|---|---|
| Re-HSA | Air | 5.76 | 0.02 |  |
|  |  | 1.27 | 0.13 |  |
|  |  | 0.053 | 0.85 | 2.75 |
|  | Argon | 6.23 | 0.03 |  |
|  |  | 1.39 | 0.11 |  |
|  |  | 0.051 | 0.87 | 3.44 |

The decays were best fit to a sum of three-exponential decay laws. The mean lifetimes are 2.75 μs in air-equilibrated and 3.44 μs in argon-equilibrated buffer solutions, respectively. The elimination of oxygen is therefore not required for use in fluorescence polarization immunoassays of high molecular weight analytes.

Figure 9:
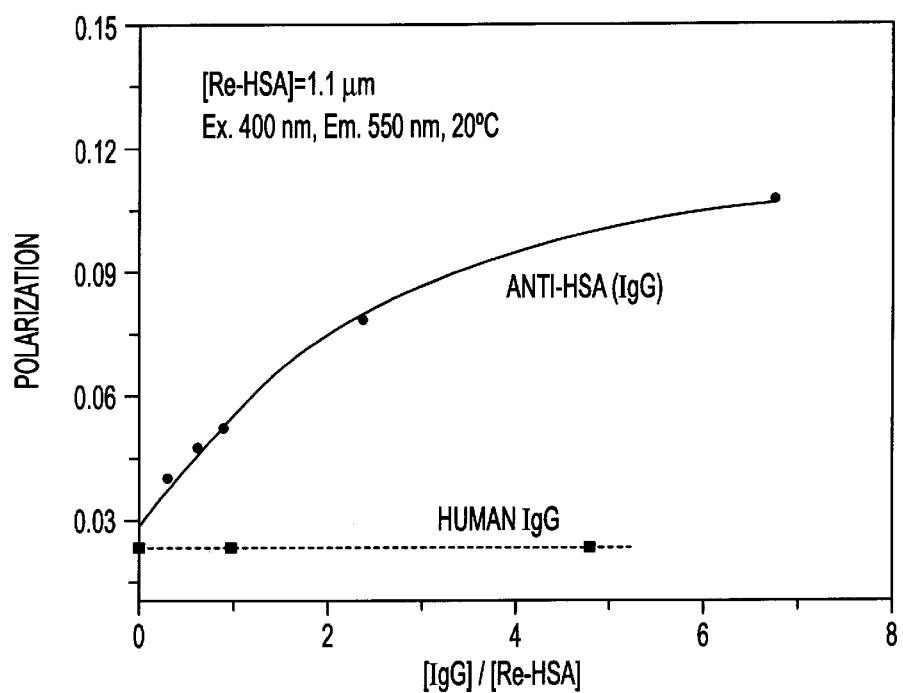
FIG. 9 graphically depicts binding of $[Re(bcp)(CO)_3(4\text{-}COOHPy)]^+$ labeled HSA to anti-HSA. The increase in polarization is due to binding of the antibody to HSA. This demonstrates the possibility of polarization immunoassays using this high quantum yield rhenium complex. The excitation wavelength was 400 nm and observation was 550 nm with a bandpass of 8 nm, at 20° C.
Figure 10A:
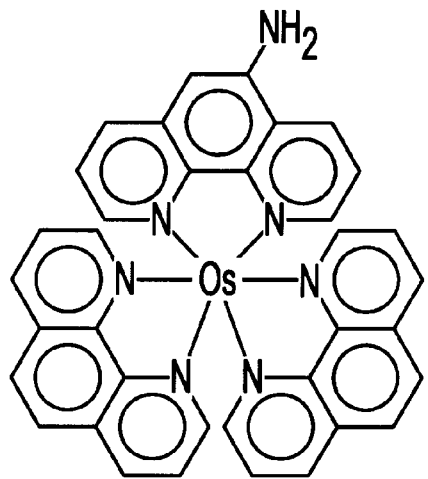
FIG. 10 shows the chemical structure of $[Os(phen)_2(aphen)]^{2+}$ and $[Os(tpy)(triphos)]^{2+}$.
Figure 10A:
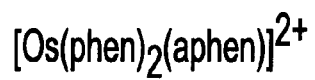
Figure 10B:
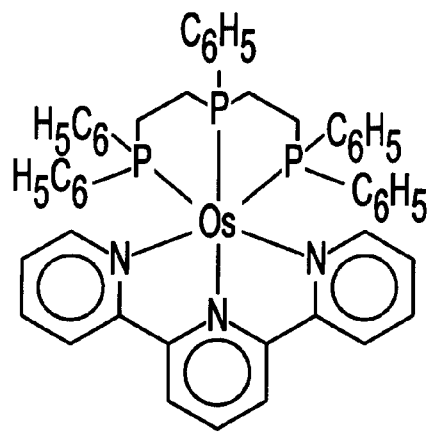
Figure 10B:

To evaluate the feasibility of using [Re(bcp)(CO)$_3$(4-COOHPy)]$^+$ in a polarization immunoassay, Re-HSA was used as an antigen. We examined the changes in anisotropy of Re-labeled HSA in the presence of increasing amounts of anti-HSA. The polarization increased about four-fold from 0.023 to 0.108 which corresponds to anisotropy values ranging between 0.017 to 0.075 (FIG. 9). Similar results were obtained using two different batches of anti-HSA with antibody (Ab) concentrations ranging from 0 to 8 times that of Re-HSA (Ag). An association constant was calculated from the data in FIG. 9 and found to be 3.3 μM$^{-1}$. We used nonspecific human IgG as a control, and no detectable changes in polarization of Re-HSA were observed in that experiment (FIG. 9).

Figure 24:
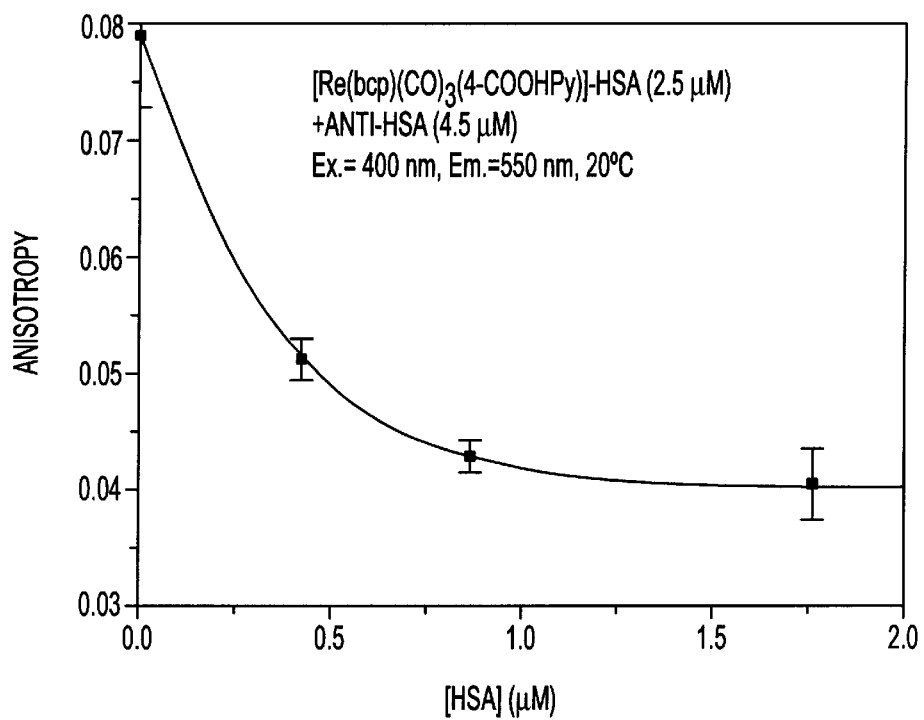
FIG. 24 graphically depicts the steady-state fluorescence polarization of Re-HSA added to preincubated mixtures of anti-HSA with various concentrations of unlabeled HSA. The excitation wavelength was 400 nm and the observation wavelength was 550 nm with a bandpass of 8 nm, at 20° C. Error bars represent the standard deviations of three polarization readings.

A competitive assay for HSA utilizes labeled and unlabeled antigens which are allowed to simultaneously compete for the binding sites on the antibody. The simultaneous exposure of the labeled and unlabeled HSA to anti-HSA resulted in a constant anisotropy at all concentrations. This may reflect a higher affinity of anti-HSA for unlabeled HSA or the formation of aggregates around the labeled antigen. However, preincubation of the unlabeled HSA with anti-HSA for 30 minutes, followed by the addition of the Re-labeled antigen, resulted in measurable changes in anisotropy. In this sequential assay, the anisotropy was found to decrease with increasing amounts of unlabeled HSA (FIG. 24). The concentrations of Re-labeled HSA and anti-HSA were 2.5 μM and 4.5 μM, respectively. At high concentrations of unlabeled HSA, the anisotropy could not be reversed to the value for unbound Re-HSA (r=0.017, p=0.023), which should be observed on total replacement of Re-HSA with unlabeled HSA. This effect could be explained by non-specific binding of Re-HSA to other proteins present in the solution. However, the polarization of Re-HSA was not influenced by the presence of non-specific proteins in the IgG ascites fluid (FIG. 9). Another reason for this behavior may be a result of a higher binding affinity for Re-HSA than for free HSA or possibly irreversible interactions between the Ab and Ag.

EXAMPLE 3

Anisotropy Probe for Protein Hydrodynamics

Human serum albumin (HSA), bovine immunoglobulin G (IgG), were obtained from Sigma Chemical Co. and were used without further purification. 2,9-dimethyl-4,7-diphenyl-1,10- phenanthroline (bcp), isonicotinic acid (4-COOHPy), AgClO$_4$, NH$_4$PF$_6$, and Re(CO)$_5$Cl were from Aldrich Chemical Co. and used as received. The other solvents used were of HPLC or spectroscopic reagent grade.

5 mg of N,N'-dicyclohexylcarbodiimide (DCC) and 3 mg of N-hydroxy-succinimide (NHS) were dissolved in 0.15 ml of DMF with stirring, 10 mg of the Re-complex in 0.15 ml of DMF was then added, and the mixture was stirred for a few hours. The formed precipitate was removed by filtration through a syringe filter, and the filtrate containing the active Re-complex was used for labeling the substrates.

The proteins HSA and IgG (10 mg of protein) were labeled by adding a 15-fold molar excess of the activated Re-complex in 50 μl of DMF to 1 ml of stirred protein solution (0.2 M carbonate buffer, pH 8.5), followed by a 5 h incubation. The conjugates were purified by gel filtration chromatography on Sephadex G-25 or G-50, using 0.1 M Na$_2$HPO$_4$ $_{-0.1}$ M NaH$_2$PO$_4$ (0.1 M PBS) buffer, pH 7.0, as eluent. The dye:protein ratios of Re-HSA and Re-IgG conjugates were determined to be 2:1 and 3:1, respectively. The concentration of protein was determined by the Coomassie Plus Protein Assay. The concentration of Re (I) complex was determined by its absorbance at 400 nm, assuming the extinction coefficient ($\epsilon_{400\ nm}$=5040 M$^{-1}$ cm$^{-1}$) was the same as that of the free dye.

Fluorescence intensity and anisotropy decays were measured by time-correlated single photon counting (TCSPC). (Birch, D. J. S., and Imhof, R. E., In *Topics in Fluorescence Spectroscopy*, Vol. 1: *Techniques*, Lakowicz, J. R., Ed., Plenum, N.Y., (1991) pp. 1–45). The light source was the output of a Pridine 1 dye laser, cavity dumped at 0.19 MHz and frequency doubled to 380 nm. For TCSPC measurements the emission was isolated using a long pass filter transmitting above 520 nm. The detector was a Hamamatau R2809 red-sensitive microchannel plate PMT.

The time-domain intensity data were fitted by the usual procedures of nonlinear least squares and were fitted to single and multi-exponential decay laws. The intensity decays were described by Equation 9. The fitting was carried out by using software from IBH Software (Edinburgh, Scotland).

The time-resolved anisotropy decays were obtained by measuring the time dependent decays of the vertically (I(t)) and horizontally (I(t)) polarized components of the emission $$r(t) = \frac{I_\|(t) - I_\perp(t)}{I_\|(t) + 2I_\perp(t)} \quad (12)$$

These data were fitted to a single and double correlation time model, using the IBH software, $$r(t) = \sum_i r_{0i} e^{-t/\theta_i} \quad (13)$$

where $r_{0\,i}$ are the amplitudes and $\theta_i$ are the rotational correlation times.

The excitation anisotropy spectra were collected as usual, with the anisotropy defined by $$r(\lambda) = \frac{I_\|(\lambda) - I_\perp(\lambda)}{I_\|(\lambda) + 2I_\perp(\lambda)} \quad (14)$$

Steady-state fluorescence data were obtained using a spectrofluorometer from SLM Instruments, with magic-angle polarizer conditions and a Hamamatsu R-928 detector. The emission spectra are uncorrected for the wavelength dependence of the detection system.

Figure 25:
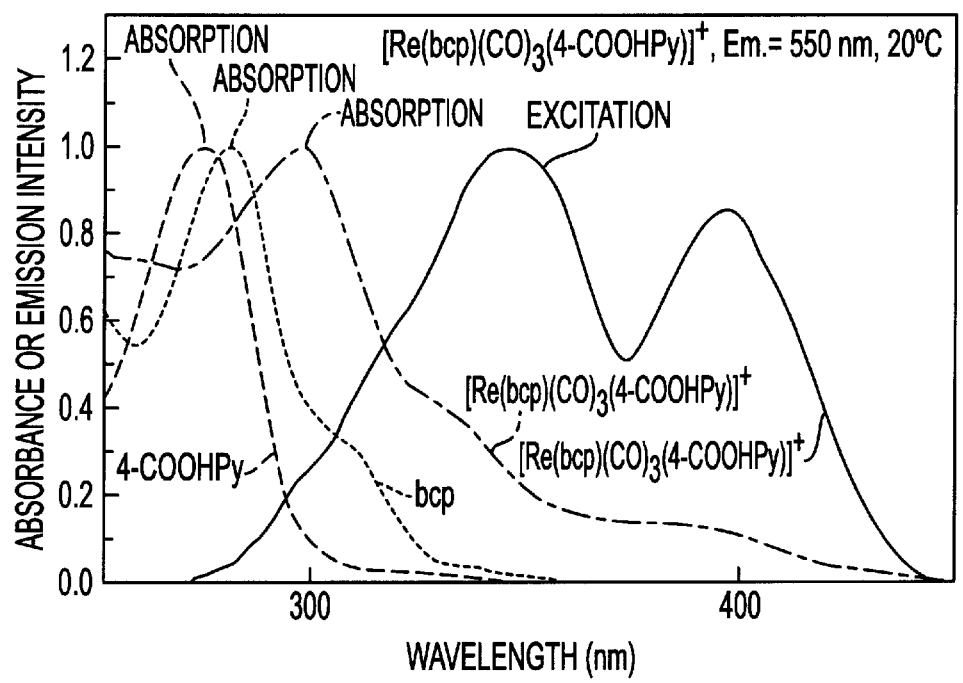
FIG. 25 shows the absorption spectra of [Re(bcp)(CO)$_3$(4-COOHPy)]$^+$, 2,9-dimethyl-4,7-diphenyl-1,10-phenanthroline (bcp), and isonicotinic acid (4-COOHPy) in methanol. The solid line shows the excitation spectrum of [Re(bcp)(CO)$_3$(4-COOHPy)]$^+$ in methanol.
Figure 26:
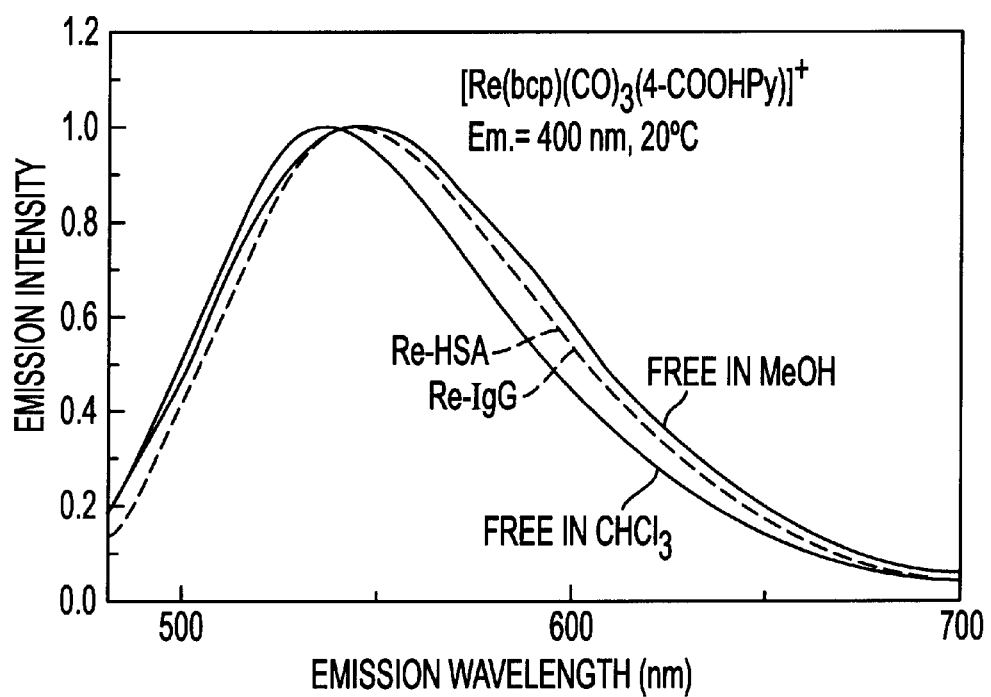
FIG. 26 depicts the intensity-normalized emission spectra of free [Re(bcp)(CO)$_3$(4-COOHPy)]$^+$ in CHCl$_3$, CH$_3$OH, and Re-labeled proteins, Re-HSA and Re-IgG in 0.1 M PBS buffer.

The molecular structure of [Re(bcp)(CO)$_3$(4-COOHPy)]$^+$ is shown in FIG. 1. The absorption and excitation spectra of the Re-complex in CH$_3$OH are shown in FIG. 25. The absorption spectra of the ligands in CH$_3$OH are also shown for comparison. The spectra are normalized to unity to facilitate comparison. The absorption spectral maxima of the low-energy absorption band around 340~450 nm and the more intense higher energy absorption at 298 nm are the characteristic metal-to-ligand charge transfer (MLCT) and π—π* absorption, respectively. The emission originates from MLCT states, with two maximal excitation bands at ~345 nm and ~390 nm, respectively. It is important to note that a complex with absorption near 380 nm can be excited with the UV output of a light emitting diode. The emission spectra of Re-complex in CHCl$_3$, CH$_3$OH and Re-HSA and Re-IgG conjugates are shown in FIG. 26. The large Stokes' shift of the Re-complex and its protein conjugates (~100 nm) makes it a good candidate for energy transfer studies and other biopysical studies as there is no possibility for self quenching. This Re-complex displays high quantum yields (>0.5) in fluid solutions at room temperature. The influence of oxygen is modest when it is bound to macromolecules.

Figure 27:
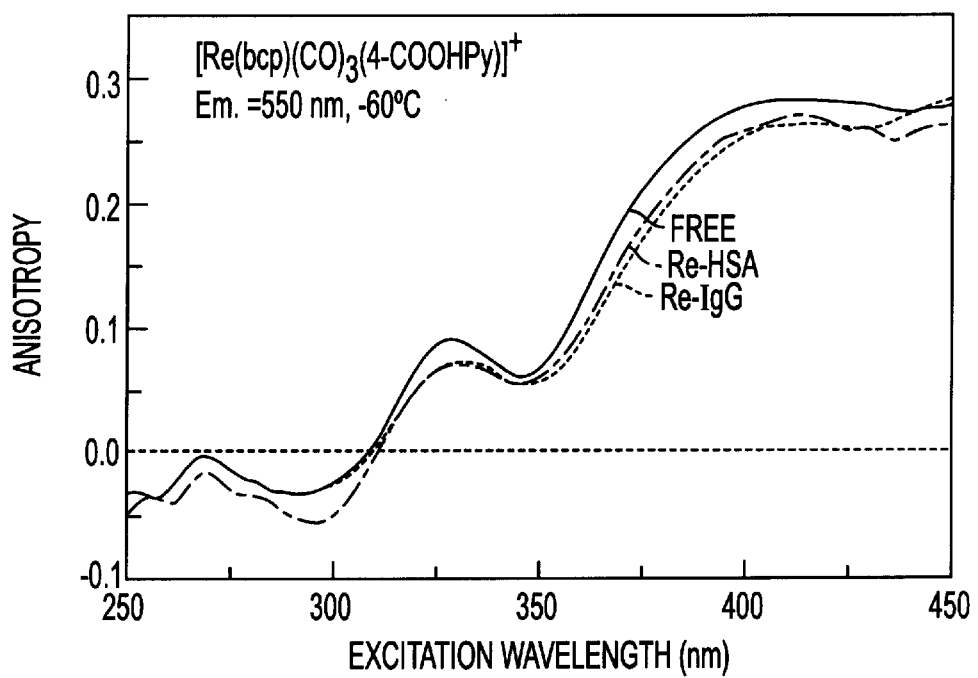
FIG. 27 graphically shows the excitation anisotropy spectra of free [Re(bcp)(CO)$_3$(4-COOHPy)]$^+$ in 100% glycerol and Re-labeled proteins in 60% glycerol/40% 0.1 M PBS buffer (v/v) with an excitation band pass of 8 nm, at −60° C.
Figure 28:
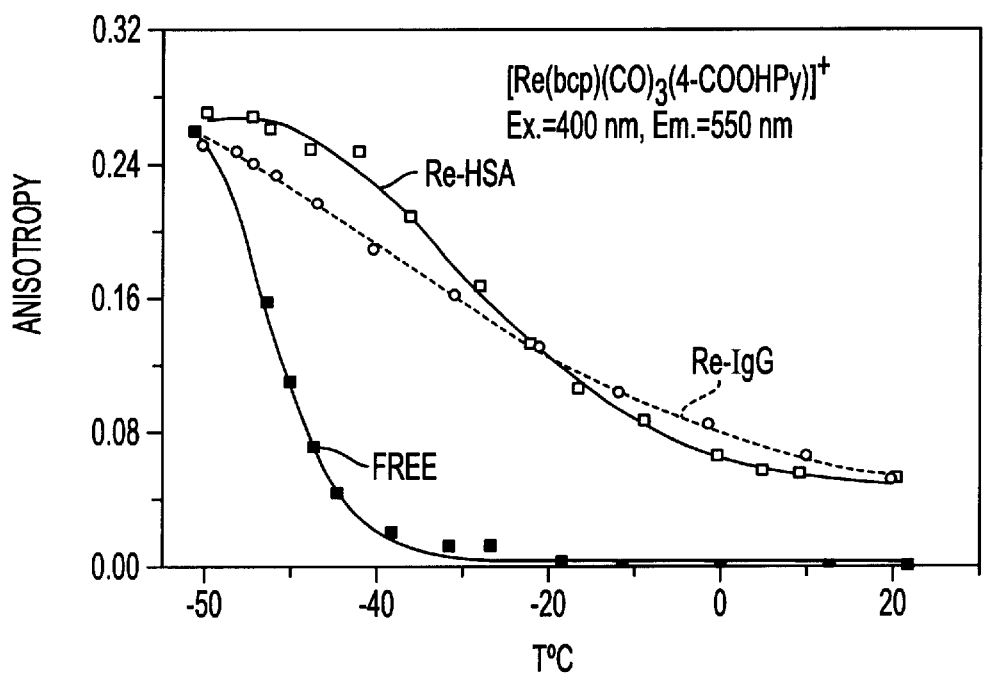
FIG. 28 depicts the temperature-dependent emission anisotropy of free [Re(bcp)(CO)$_3$(4-COOHPy)]$^+$ and its protein conjugates in 60% glycerol/40% 0.1 M PBS buffer (v/v). Excitation wavelength was 400±4 nm; emission wavelength was 550±4 nm.

To be useful as an anisotropy probe for study of macromolecular dynamics, the Re-complex needs to display polarized emission. We studied the polarized emission in the absence of rotational diffusion. The excitation anisotropy spectra of [Re(bcp)(CO)$_3$(4-COOHPy)]$^+$ and its protein conjugates, Re-HSA and Re-IgG, are shown in FIG. 27. In the absence of rotational motion, this complex shows maximal anisotropies near 0.3 and these high anisotropies are broadly available from 390 nm to 450 nm. The steady-state anisotropy of [Re(bcp)(CO)$_3$(4-COOHPy)]$^+$ and its conjugates were measured as a function of temperatures and/or viscosities (FIG. 28). The solvent used for this study was 60% glycerol/40% buffer (v/v), which formed a highly viscous solution at −60° C. The results show that the anisotropy values are nearly the same for the free dye and the Re-protein conjugates at −60° C. The steady-state anisotropy of the free [Re(bcp)(CO)$_3$(4-COOHPy)]$^+$ decreases rapidly as the temperatures are changed from low temperature, −60° C. towards high temperature, 20° C., whereas the anisotropies of Re-HSA and Re-IgG decrease more slowly with temperature, and remain adequate for measurement at room temperature. These results demonstrate that the anisotropies are sensitive to rotational motion, and the anisotropy of the Re-protein conjugates is lost by fast motions of the probe in addition to rotational motion of the proteins. Importantly, the anisotropies of the labeled protein are always larger than that of free dye, indicating that protein hydrodynamics contributes to the anisotropy.

Figure 29:
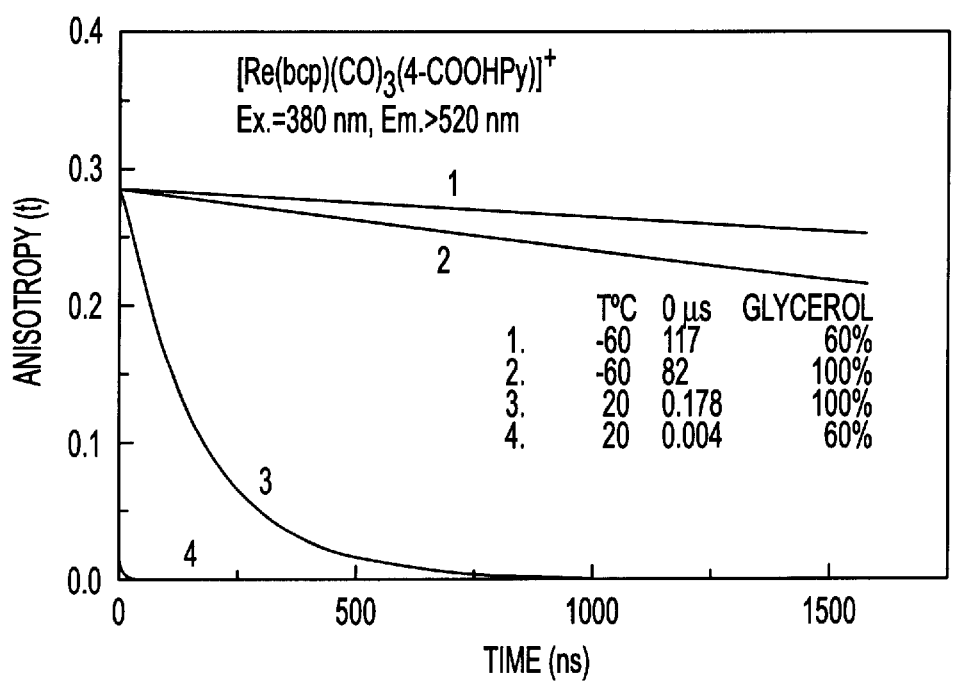
FIG. 29 shows the anisotropy decays of free [Re(bcp)(CO)$_3$(4-COOHPy)]$^+$ at the indicated solutions and the indicated temperatures.

To further demonstrate that the anisotropy depends on rotational diffusion we examined the time-dependent anisotropy of free [(Re(bcp)(CO)$_3$(4-COOHPy)]$^+$ in 100% glycerol and 60% glycerol/40% buffer (v/v) at −60° C. and 20° C. At 20° C., the anisotropy decays rapidly with a correlation time near 4 ns in 60% glycerol/40% buffer (v/v), whereas the anisotropy decays more slowly with a correlation time of 118 ns in 100% glycerol. At −60° C., the anisotropy decays much more slowly with a correlation time 82 μs in 100% glycerol (FIG. 29).

Figure 30A:
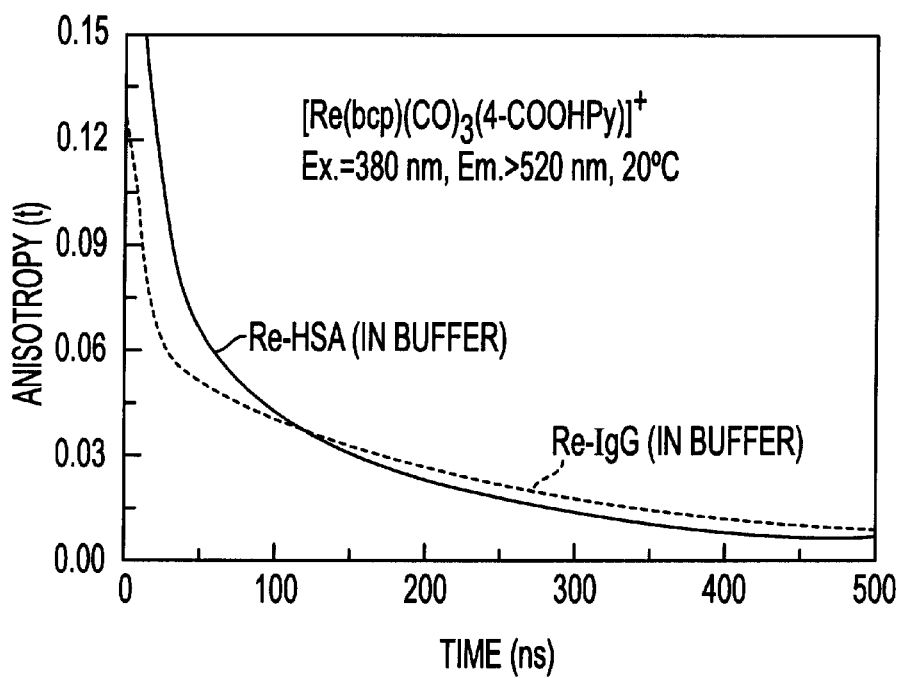
FIG. 30 graphically shows the anisotropy decays of Re-labeled proteins in buffer (top) and in the indicated solutions (bottom).
Figure 30B:
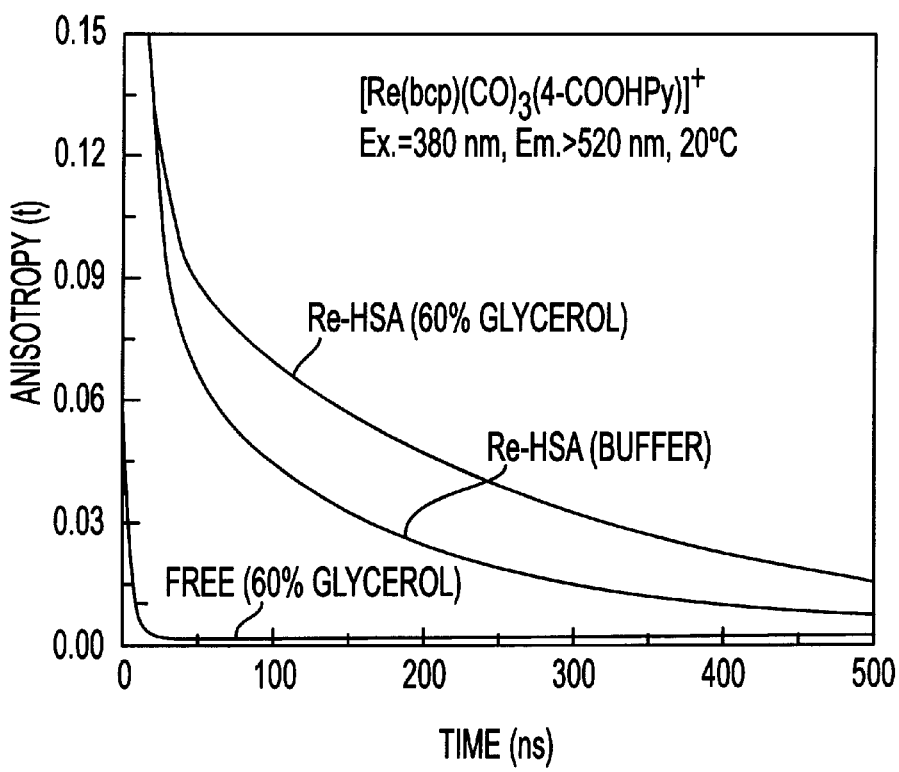

Time-resolved anisotropy decays of Re-protein conjugates are shown in FIG. 30. Analysis of these anisotropy decays are summarized in Table 3.

TABLE 3

Time-resolved Intensity Decay (τ), Rotational Correlation Times (θ) of free [Re(bcp)(CO)$_3$(4-COOHPy)]$^+$ and its protein conjugates

| Sample | $\tau_i$ (ns) | $f_i$* | $\chi_R^2$ | $\theta_i$ (ns) | $r_{io}$ | $\chi_R^2$ |
|---|---|---|---|---|---|---|
| ReCOOH in 60% glycerol | 1478 | 1 | 1.2 | 4 | 0.0713 | 0.97 |
| RE-HSA in 60% glycerol | 7 | 0.0024 |  | 12 | 0.168 |  |
|  | 79 | 0.021 |  | 457 | 0.0789 | 1.0 |
|  | 1402 | 0.98 | 1.1 |  |  |  |
| Re-HSA in 30% glycerol | 10 | 0.0089 |  | 12 | 0.157 |  |
|  | 952 | 0.93 |  | 282 | 0.104 | 1.0 |
|  | 1068 | 0.063 | 1.1 |  |  |  |
| Re-HSA in buffer | 18 | 0.02 |  | 16 | 0.143 |  |
|  | 781 | 0.84 |  | 164 | 0.0788 | 1.2 |
|  | 143 | 0.14 | 1.2 |  |  |  |
| Re-IgG in 60% glycerol | 14 | 0.0014 |  | 6 | 0.0614 |  |
|  | 1986 | 0.97 |  | 379 | 0.0384 | 2.0 |
|  | 153 | 0.025 | 1.0 |  |  |  |
| Re-IgG in buffer | 21 | 0.0088 |  | 10 | 0.0800 |  |
|  | 606 | 0.86 |  | 271 | 0.0595 | 1.2 |
|  | 134 | 0.13 | 1.1 |  |  |  |

$$*f_i = \frac{\alpha_i \tau_i}{\sum_i \alpha_i \tau_i}$$

Free [Re(bcp)(CO)$_3$(4-COOHPy)]$^+$ anisotropy decay are fitted to single exponential anisotropy decay model, whereas the anisotropy decays of Re-labeled protein are fitted to a double exponential decay model, reflecting fast motion of the probe and a slower protein rotational diffusion. In addition, the anisotropy decay of labeled IgG appears to be somewhat more complex than labeled HSA, suggesting that independent domain motions of IgG contribute to the anisotropy decay. The results demonstrate that the anisotropy decays are dependent on protein rotational diffusion and inter-domain dynamics. The anisotropy decays are slowed by adding glycerol as a result of the slower protein rotational diffusion.

EXAMPLE 4
Red Fluorescent Dyes for Biophysics and for Sensors

All chemicals and solvents were purchased from Aldrich Chemical Co. and used without further purification. The ligand tppz was purchased from GF Chemicals and recrystallized before use, and ligands ttpy (Spahni, W. And Galzaferri, G. *Helv. Chim.Acta.,* 1984, 67, 450; Constable, E. C. and Thomson, A. M., *J. Chem. Soc., Dalton Trans.* (1994) 2947) and mcbpy (Strouse, G. F., Schoonover, J. R., Duesing, R., Boyed, S., Jones, W. E. Jr., Meyer, T. J., *Inorg. Chem.,* 1995, 34, 473) were synthesized using reported procedures.

All absorbence spectra were recorded on a Hewlett Packard diode array (HP 8453) spectrophotometer. All emission spectra were recorded on a SLM AB2 spectrophotometer. The excitation anisotropy spectra were measured at −55° C. in 9:1, glycerol:methanol by weight, using a SLM 800 spectrophotometer. Excitation anisotropy spectra were collected as usual, where the anisotropy defined by Equation 5, where $I_\parallel$ and $I_\perp$ are the intensities measured with vertically polarized excitation and the emission polarization parallel ($\parallel$) or perpendicular ($\perp$) to the excitation. The values of the polarized intensities were corrected for the transmission efficiency for the polarized components by the detection optics. The reported emission spectra are corrected for variation in the detector efficiency with observation wavelength.

Fluorescence intensity decays were measured with frequency-domain instrumentation (Laczko, G. Grycznski, I., Wiczk, W., Malak, H. and Lakowicz, J. R., *Rev. Sci. Instrum.* 1990, 61, 2331). The excitation wavelength was 488 nm using an air cool argon laser supplied by Omnichrome Inc. The frequency-domain data were used to determine the intensity decay law using multiexponential model $$I(t) = \sum_{i=1}^{n} \alpha_i e^{-t/\tau_I} \qquad (15)$$

where $\alpha_i$ are the preexponential factors, $\tau_i$ are decay times, and n is the number of exponential components. The mean decay time is given by $$\bar{\tau} = \alpha_i \tau_i^2 / \sum \alpha_j \tau_j \qquad (16)$$

Synthesis of Complexes

All of these complexes were synthesized as $PF_6$ salts by following two different methods which depend on the ligand used. Method A describes the synthesis of complexes using tridentate ligands (L—L—L) generally ttpy, tpy, tppz and triphos. Method B describes the synthesis of complexes using bidentate ligands (L—L) which are consist of mcbpy, phen and aphen ligands. Both methods are modifications of reported methods (Kober, E. M., Marshall, J. L., Dressick, W. J., Sullivan, B. H., Casper, J. V. and Mayer, T. J. *Inorg. Chem.,* (1984) 24, 2755; Brewer, R. G., Jensen, G. E. and Brewer, K. J. *Inorg. Chem.,* (1994) 33, 124; Kober, E. M., Marshall, J. L., Dressick, W. J., Sullivan, B. H., Casper, J. V. and Meyer, T. J. *J. Am. Chem. Soc.,* (1980) 102, 7385; Arana, C. R. and Abruna, H. O. *Inorg. Chem.* (1993) 32, 194; Sauvage, J. P., Collin, J. H., Chambron, J. C., Guillerez, S.Coudret, C., Balzani V., Bariegelleti, F., Cola, L. D., and Flamigni, L., *Chem. Rev.* (1994) 94, 993).

Synthesis of $[Os(L—L—L)_3]^{2+}$, with Tridentate Ligands (Method A)

In this typical synthesis, one equivalent of $OsCl_3$ and one equivalent of tridentate ligands, L—L—L, (where L—L—L is either ttpy, tppz or triphos) was heated at reflux in 100 ml of ethanol, and a black precipitate of $Os(L—L—L)Cl_3$ forms after three hours of heating. This precipitate was filtered after cooling and washed with water and ethanol. This is the starting material for the desired compounds, $[Os(L—L—L)_3]^{2+}$, Equal molar ratios of $Os(L—L—L)Cl_3$ and the appropriate ligand were further heated at reflux in 20 ml of ethylene glycol for one hour, which produces a brown solution. After cooling, about 100 ml of a saturated solution of ammonium hexafluorophosphate in water was added. After a few minutes, a dark brown-black precipitate formed. This precipitate was separated out by vacuum filtration and dried. All these compounds were recrystallized after dissolving them in acetonitrile and crystallizing them by using an excess amount of ether. They were chromatographed on neutral alumina using a 5:2 toluene:acetonitrile mixture.

Synthesis of $[Os(L—L)_3]^{2+}$, with Bidentate Ligands (Method B)

The starting material, $Os(L—L)_2Cl_2$, for all these compounds was synthesized by mixing one equivalent of $(NH_4)_2OsCl_6$ and two equivalents of bidentate ligands L—L, (where L—L are either mcbpy, phen or aphen). This reaction mixture was heated at reflux for about one hour in 50 ml of ethylene glycol. A dark brown precipitate was obtained which was filtered and washed with water and ethanol. For making $[Os(L—L)_3]^{2+}$ complexes, equal molar ratios of $Os(L—L)_2Cl_2$ and the appropriate ligand were further heated at reflux in 20 ml of ethylene glycol for about six hours, which produced a greenish brown solution. After cooling this reaction mixture, about 100 ml of a saturated solution of ammonium hexafluorophosphate in water was added, and a dark green precipitate separated out. The precipitate was filtered by vacuum filtration and dried. These dried compounds were recrystallized by dissolving them in acetonitrile and crystallizing them out by adding a large amount of ether. It was chromatographed on neutral alumina using a 2:1 toluene:acetonitrile mixture.

Electronic Absorption Spectroscopy

Figure 11:
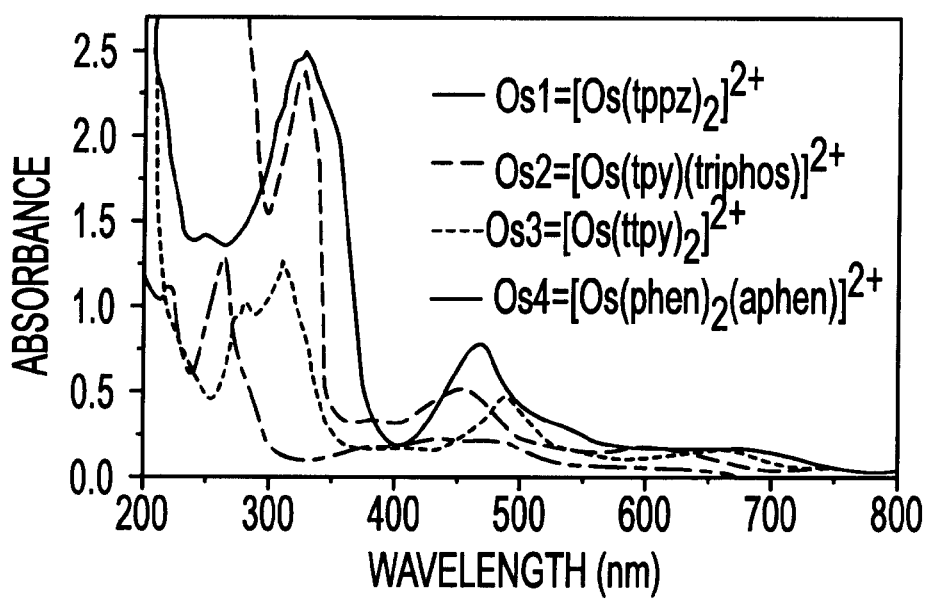
FIG. 11 graphically depicts the absorption spectra of red absorbing osmium probes in acetonitrile at room temperature.

The electronic spectra of these osmium complexes in acetonitrile are shown in FIG. 11 and summarized in Table 4.

TABLE 4

Spectral properties of the red osmium probes

| Probes[a] | $\lambda_{max}^{abs}$ (nm)[b] | $\lambda_{max}^{em}$ (nm)[b] | $\tau(ns)^c$ | $\phi^c$ | $r_o^d$ |
|---|---|---|---|---|---|
| $[Os(ttpy)_2]^{2+}$ | 500 | 735 | 220 | 0.02 | 0.15 |
| $[Os(3,2,1)]^{2+}$ | 550 | 640 | 130 | 0.015 | — |
| $[Os(tpy)(triphos)]^{2+}$ | 470 | 710 | 230 | — | 0.35 |
| $[Os(phen)_2(aphen)]^{2+}$ | 485 | 700 | 195 | 0.02 | 0.02 |
| $[Os(tppz)_2]^{2+}$ | 480 | 740 | 175 | 0.016 | 0.18 |

[a]All are $PF_6$ salts;
[b]measured in acetonitrile;
[c]measured in deoxygenated acetonitrile;
[d]measured in 9:1 glycerol:methanol mixture at −55° C.

The ultraviolet region of the tridentate ligands are similar to each other and are dominated by the $\pi \rightarrow \pi^*$ transitions from the ligand. The visible region of the electronic spectra of tridentate complexes contains intense bands centered between 450–500 nm. These transitions represent the lowest lying $^1$MLCT, which is Os(dπ)-L—L—L(π*) in nature for all these complexes. Due to the high degree of spin-orbit coupling in osmium, transitions that are formally spin forbidden exhibit enhanced intensity. (650 nm). These MLCT transitions appear as tails on the low energy end of the more intense $^1$MLCT transition.

Emission Spectroscopy, Quantum Yields and Excited State Lifetimes

Figure 12:
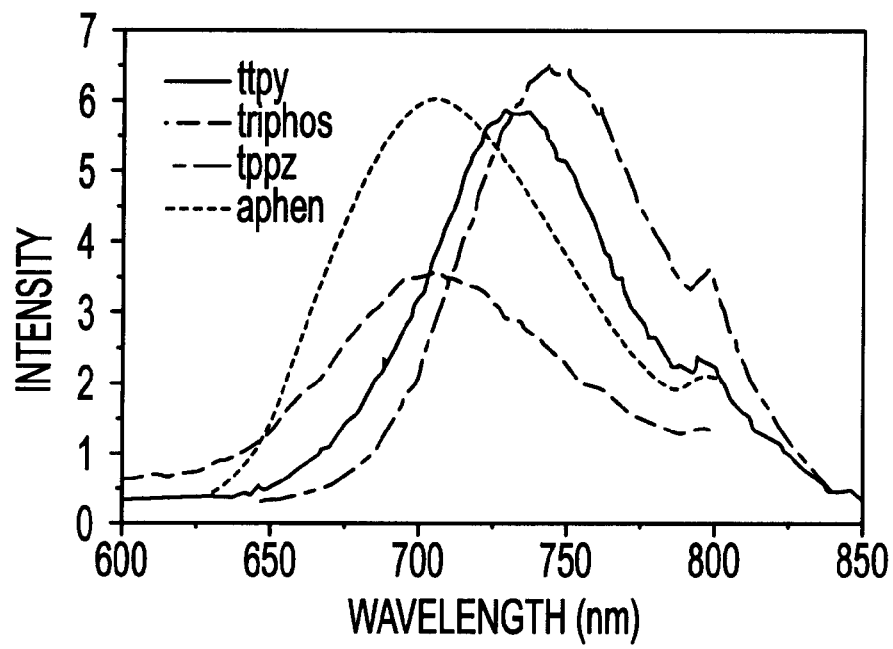
FIG. 12 graphically shows the emission spectra of $[Os(phen)_2(aphen)]^{2+}$, $[Os(tpy)(triphos)]^{2+}$, $[Os(tppz)_2]^{2+}$, and $[Os(ttpy)_2]^{2+}$.

The emission maxima, quantum yields, and lifetimes are outlined in Table 4. All these complexes emit at 700–750 nm at room temperature, FIG. 12, when they are excited at 480 to 550 nm. Similar trends are seen in the emission and absorption energies of all these complexes. All of these complexes have excited-state lifetimes around 200 ns. The lifetime of the $[Os(tppz)_2]^{2+}$ complex was found to be 175 ns. The quantum yields of all these complexes are around 2 percent which is typical for all these red emitting osmium(II) complexes (Kober, E. M., Marshall, J. L., Dressick, W. J., Sullivan, B. H., Casper, J. V. and Mayer, T. J. *Inorg. Chem.*, (1984) 24, 2755; Sauvage, J. P., Collin, J. H., Chambron, J. C., Guillerez, S. Coudret, C., Balzani, V., Barigelleti, F., Cola, L. D., and Flamigni, L., *Chem. Rev.* (1994) 94, 993).

Fundamental Anisotropy ($r_0$).

Figure 13:
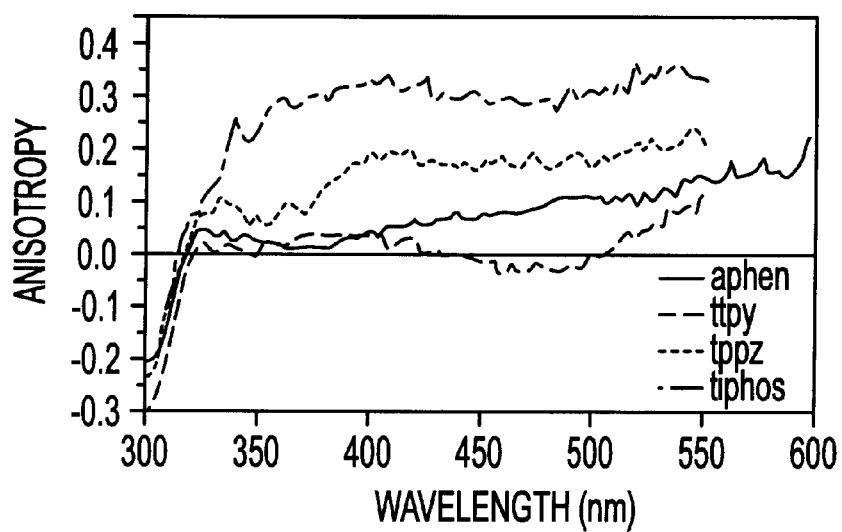
FIG. 13 is a graph depicting the anisotropy spectra of $[Os(phen)_2(aphen)]^{2+}$, $[Os(tpy)(triphos)]^{2+}$, $[Os(tppz)_2]^{2+}$, and $[Os(ttpy)_2]^{2+}$ in 9:1 glycerol:methanol at −55° C.

Anisotropy of these complexes are measured in 9:1 (glycerol:methanol by weight) at −55° C. and summarized in Table 4, and shown in FIG. 13. The trend of the anisotropy depends on the structure of the molecules. More asymmetric molecules show higher anisotropies. The complex [Os(tpy)(triphos)]$^{2+}$ is the most asymmetric molecule, and therefore shows a high anisotropy value (0.35).

Since many modifications, variations, and changes in detail may be made to the described embodiments, it is intended that all matter in the foregoing description and shown in the accompanying drawings be interpreted as illustrative and not in a limiting sense.

What is claimed is:

1. A method of conducting an assay of a sample containing an analyte of interest, comprising the steps of:
   forming a mixture so as to bring a metal-ligand complex into interactive proximity with said sample containing said analyte of interest;
   irradiating said mixture with electromagnetic light energy so as to cause emission of light indicative of said analyte of interest; and
   measuring the emitted light and utilizing the measurement of the emitted light so as to measure the analyte of interest, wherein said metal-ligand complex is selected from the group consisting of $[Re(bcp)(CO)_3(4-COOHPy)]^+$, $[Os(phen)_2(aphen)]^{2+}$, $[Os(tpy)(triphos)]^{2+}$, and $[Os(ttpy)_2]^{2+}$.

2. A method as defined by claim 1, wherein said assay is used to characterize a high molecular weight antigen.

3. A method as defined by claim 2, wherein said analyte of interest is human serum albumin.

4. A method as defined by claim 1, wherein said assay is used to characterize protein hydrodynamics.

5. A method as defined by claim 4, wherein said analyte of interest is human serum albumin and bovine immunoglobin G.

6. A method as defined by claim 1,
   wherein said assay is used to characterize a sample lipid; and
   wherein said metal-ligand complex is coupled to a lipid so as to form a lipid-metal-ligand complex.

7. A method as defined by claim 1, wherein said analyte is oxygen.

8. A method as defined by claim 1,
   wherein said assay is used to quantify said analyte of interest;
   wherein prior to said forming step, a first binding partner and a second binding partner are added to said sample, wherein said first binding partner competes with the analyte for binding to said second binding partner, wherein one of said first and second binding partner is labeled with a metal-ligand complex and the other is labeled with a photoluminescent energy transfer acceptor, wherein the metal-ligand complex and photoluminescent energy transfer acceptor are chosen such that when the first binding partner binds to the second binding partner, the metal-ligand complex and the photoluminescent energy transfer acceptor are brought into interactive proximity, producing a detectable change in luminescence.

9. A method as defined by claim 8,
   wherein subsequent to said measuring step, binding of the first binding partner to the second binder partner is quantified; and
   wherein said binding is quantified by a method from the group consisting of intensity, lifetime, and polarization, thereby quantifying the analyte.

10. A method as defined by claim 1, wherein fluorescence lifetime is measured.

11. A method as defined by claim 1, wherein said metal-ligand complex is coupled to said analyte of interest.

12. A method as defined by claim 1, wherein said metal-ligand complex is substituted with a functional group that can be directly conjugated to macromolecules selected from the group consisting of amine reactive N-hydroxysuccimide, isothiocyanate, sulfonyl chloride containing ligands, sulfhydryl reactive iodoacetadmide, and maleimide containing ligands.

13. A method as defined by claim 1,
   wherein said electromagnetic light energy is linearly polarized light energy; and
   wherein polarization of the emitted light is measured.

14. A method as defined by claim 13, wherein said linearly polarized light energy has a wavelength of about 400.

15. A method as defined by claim 13, wherein said linearly polarized high energy has a wavelength from 280 to 1100 nm.

* * * * *